United States Patent
Gangaraju

(10) Patent No.: US 10,132,815 B2
(45) Date of Patent: Nov. 20, 2018

(54) METHODS OF DIAGNOSING, TREATING AND MONITORING DIABETIC RETINOPATHY

(71) Applicant: Shekhar Raja Gangaraju, Avon, IN (US)

(72) Inventor: Shekhar Raja Gangaraju, Avon, IN (US)

(73) Assignee: Indiana University Research & Technology Corporation, Indianapolis, IN (US)

(*) Notice: Subject to any disclaimer, the term of this patent is extended or adjusted under 35 U.S.C. 154(b) by 0 days.

(21) Appl. No.: 14/767,111

(22) PCT Filed: Feb. 7, 2014

(86) PCT No.: PCT/US2014/015257
§ 371 (c)(1),
(2) Date: Aug. 11, 2015

(87) PCT Pub. No.: WO2014/126796
PCT Pub. Date: Aug. 21, 2014

(65) Prior Publication Data
US 2015/0377908 A1 Dec. 31, 2015

Related U.S. Application Data

(60) Provisional application No. 61/763,993, filed on Feb. 13, 2013.

(51) Int. Cl.
| | |
|---|---|
| *A61K 39/395* | (2006.01) |
| *G01N 33/68* | (2006.01) |
| *C07K 16/24* | (2006.01) |
| *C07K 14/52* | (2006.01) |
| *C12N 15/113* | (2010.01) |

(52) U.S. Cl.
CPC ......... *G01N 33/6893* (2013.01); *C07K 14/52* (2013.01); *C07K 16/24* (2013.01); *C12N 15/1136* (2013.01); *G01N 33/6863* (2013.01); *C07K 2317/76* (2013.01); *C12N 2310/14* (2013.01); *C12N 2320/30* (2013.01); *G01N 2333/52* (2013.01); *G01N 2800/164* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,382,316 B2 * | 7/2016 | Yoon | C07K 16/18 |
| 9,452,200 B2 * | 9/2016 | Wells | A61K 38/195 |
| 2012/0087928 A1 | 4/2012 | Lashkari | |
| 2012/0195906 A1 | 8/2012 | Clauss et al. | |

FOREIGN PATENT DOCUMENTS

WO    WO1997010841    *    3/1997

OTHER PUBLICATIONS

Zohlnhofer et al. Rapamycin Effects Transcriptional Programs in Smooth Muscle Cells Controlling Proliferative and Inflammatory Properties. Molecular Pharmacology (2004), 65(4), 880-889.*
Nuhrenberg et al. EMAP-II downregulation contributes to the beneficial effects of rapamycin after vascular injury. Cardiovascular Research (2008) 77, 580-589.*
Hou et al. Endothelial-monocyte-activating polypeptide II induces migration of endothelial progenitor cells via the chemokine receptor CXCR3. Experimental Hematology 34 (2006) 1125-1132.*
Yuan et al. Blockade of EMAP II Protects Cardiac Function after Chronic Myocardial Infarction by Inducing Angiogenesis. J Mol Cell Cardiol. Feb. 2015 ; 79: 224-231.*
Dorofeyeva et al. Endothelial monocyte-activating polypeptide-II improves heart function and endothelium-dependent relaxation of aorta in type 1 diabetes mellitus, EASD 2016. Abstract meeting.*
Dugel et al. A Randomized, Dose-Escalation Study of Subconjunctival and Intravitreal Injections of Sirolimus in Patients with Diabetic Macular Edema (Ophthalmology, Jan. 2012;119:124-131).*
Mohylnytska LA. Serum levels of endothelial monocyte-activating polypeptide-II in type 2 diabetes mellitus. Fiziol Zh. 2014;60(1):84-90. Abstract.*
Fauser et al. Differential activation of microglial cells in local and remote areas of IRBP1169-1191-induced rat uveitis. Acta Neuropathol (2001) 101 :565-571.*
Daemen et al. Inhibition of apoptosis induced by ischemia-reperfusion prevents inflammation. J. Clin. Invest. 104:541-549 (1999).*
Zheng et al. Retinal Ischemia and Reperfusion Causes Capillary Degeneration: Similarities to Diabetes. Invest Ophthalmol Vis Sci. 2007;48:361-367.*
International Search Report and Written Opinion dated Aug. 8, 2014, in connection with PCT/US2014/015257.
Murdoch et al., "Mechanisms regulating the recruitment of macrophages into hypoxic areas of tumors and other ischemic tissues," Blood, Oct. 15, 2014, vol. 104, No. 8, pp. 2224-2234.

* cited by examiner

*Primary Examiner* — Maher M Haddad
(74) *Attorney, Agent, or Firm* — Quarles & Brady LLP

(57) ABSTRACT

Methods for the treatment and monitoring of diabetic retinopathy are provided. More specifically, the method for the treatment of diabetic retinopathy comprises administering to an individual suspected of having diabetic retinopathy a composition comprising an agent that inhibits the activity or expression of EMAPII or CXCR3. Methods for diagnosing and monitoring the progression of diabetic retinopathy in an individual, or monitoring the efficacy of a therapy for diabetic retinopathy are provided. More specifically, the method comprises determining the levels of EMAPII in a biological sample from an individual and comparing them to a control or reference sample, or a chronological sample from the individual.

2 Claims, 13 Drawing Sheets

Specification includes a Sequence Listing.

α-tubulin
EMAPII
DAPI

SEQUENCE LISTING

```
<160> NUMBER OF SEQ ID NOS: 15

<210> SEQ ID NO 1
<211> LENGTH: 354
<212> TYPE: DNA
<213> ORGANISM: Artificial Sequence
<220> FEATURE:
<223> OTHER INFORMATION: synthetic

<400> SEQUENCE: 1
gcggtgcacc ttgttgagtc tggtggagga tttgtgcagc ctacggagtc attgaaaatc      60
tcatgtgcag cctctggatt caccttcagt gatgctgcca tgtactgggt ccgccaggct     120
ccaggaaagg gtctggaatg ggttgctcgc ataagaacta aacctaataa ttatgccaca     180
tattatgctg attcagtgaa aggcagattc accatctccc gagatgattc aaaaagcatg     240
gtctacctac aaatggataa cttgaaaact gaggacacag ccatgtatta ctgtacatca     300
tggagctacg actttgatta ctggggccaa ggagtcatgg tcacagtctc ctca           354

<210> SEQ ID NO 2
<211> LENGTH: 118
<212> TYPE: PRT
<213> ORGANISM: Artificial Sequence
<220> FEATURE:
<223> OTHER INFORMATION: synthetic

<400> SEQUENCE: 2

Ala Val His Leu Val Glu Ser Gly Gly Gly Phe Val Gln Pro Thr Glu
1               5                   10                  15

Ser Leu Lys Ile Ser Cys Ala Ala Ser Gly Phe Thr Phe Ser Asp Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Tyr Tyr Ala Asp
    50                  55                  60

Ser Val Lys Gly Arg Phe Thr Ile Ser Arg Asp Asp Ser Lys Ser Met
65                  70                  75                  80
```

```
Val Tyr Leu Gln Met Asp Asn Leu Lys Thr Glu Asp Thr Ala Met Tyr
                85                  90                  95

Tyr Cys Thr Ser Trp Ser Tyr Asp Phe Asp Tyr Trp Gly Gln Gly Val
            100                 105                 110

Met Val Thr Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: synthetic

<400> SEQUENCE: 3

Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Ser Gly Lys Thr Tyr Leu Asn Trp Tyr Leu Gln Arg Pro Gly Gln Ser
        35                  40                  45

Pro His Leu Leu Ile Tyr Gln Met Ser Thr Arg Ala Ser Gly Val Ser
    50                  55                  60

Asp Arg Leu Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Gln Gln Phe
                85                  90                  95

Leu Glu Tyr Pro Leu Thr Phe Gly Ser Gly Thr Lys Leu Glu Ile Lys
            100                 105                 110

<210> SEQ ID NO 4
<211> LENGTH: 338
<212> TYPE: DNA
<213> ORGANISM: Artificial Sequence
<220> FEATURE:
<223> OTHER INFORMATION: synthetic

<400> SEQUENCE: 4
gatattgtga tgacccaggg tgcactcccc aaccctgtcc cctctggaga gtcagcttcc      60
atcacctgcc agtctagtaa gagtctgctg cacagcagtg gcaagacata cttgcaattg     120
gtatctgcag aggccaggac agtctcctca tctcctgatc tattggatgt ccacccgtgc     180
atcaggagtc tcagacaggc tcagtggcag tgggtcagga acagatttca cactgaaaat     240
cagcagcgtg gaggctgagg atgtgggtgt gtattactgt cagcaatttc tagagtatcc     300
tctcacgttc ggttctggga ccaagctgga gatcaaac                             338

<210> SEQ ID NO 5
<211> LENGTH: 8
<212> TYPE: PRT
<213> ORGANISM: Artificial Sequence
<220> FEATURE:
<223> OTHER INFORMATION: synthetic

<400> SEQUENCE: 5

Gly Phe Thr Phe Ser Asp Ala Ala
1               5

<210> SEQ ID NO 6
<211> LENGTH: 10
```

```
<212> TYPE: PRT
<213> ORGANISM: Artificial Sequence
<220> FEATURE:
<223> OTHER INFORMATION: synthetic

<400> SEQUENCE: 6

Ile Arg Thr Lys Pro Asn Asn Tyr Ala Thr
1               5                   10

<210> SEQ ID NO 7
<211> LENGTH: 9
<212> TYPE: PRT
<213> ORGANISM: Artificial Sequence
<220> FEATURE:
<223> OTHER INFORMATION: synthetic

<400> SEQUENCE: 7

Thr Ser Trp Ser Tyr Asp Phe Asp Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: synthetic

<400> SEQUENCE: 8

Lys Ser Leu Leu His Ser Ser Gly Lys Thr Tyr
1               5                   10

<210> SEQ ID NO 9
<211> LENGTH: 3
<212> TYPE: PRT
<213> ORGANISM: Artificial Sequence
<220> FEATURE:
<223> OTHER INFORMATION: synthetic

<400> SEQUENCE: 9

Trp Met Ser
1

<210> SEQ ID NO 10
<211> LENGTH: 9
<212> TYPE: PRT
<213> ORGANISM: Artificial Sequence
<220> FEATURE:
<223> OTHER INFORMATION: synthetic

<400> SEQUENCE: 10

Gln Gln Phe Leu Glu Tyr Pro Leu Thr
1               5

<210> SEQ ID NO 11
<211> LENGTH: 68
<212> TYPE: PRT
<213> ORGANISM: Artificial Sequence
<220> FEATURE:
<223> OTHER INFORMATION: synthetic

<400> SEQUENCE: 11

Gln Gln Ser Ile Ala Gly Ser Ala Asp Ser Lys Pro Ile Asp Val Ser
1               5                   10                  15

Arg Leu Asp Arg Ile Gly Cys Ile Ile Thr Ala Arg Lys His Pro Asp
                20                  25                  30

Ala Asp Ser Leu Tyr Val Glu Glu Val Asp Val Gly Glu Ile Ala Pro
```

```
                35                  40                  45
Arg Thr Val Val Ser Gly Leu Val Asn His Val Pro Leu Glu Gln Met
        50                  55                  60

Gln Asn Arg Met
65
```

<210> SEQ ID NO 12
<211> LENGTH: 17
<212> TYPE: PRT
<213> ORGANISM: Artificial Sequence
<220> FEATURE:
<223> OTHER INFORMATION: synthetic

<400> SEQUENCE: 12

```
Gln Gln Ser Ile Ala Gly Ser Ala Asp Ser Lys Pro Ile Asp Val Ser
1               5                   10                  15

Arg
```

<210> SEQ ID NO 13
<211> LENGTH: 17
<212> TYPE: PRT
<213> ORGANISM: Artificial Sequence
<220> FEATURE:
<223> OTHER INFORMATION: synthetic

<400> SEQUENCE: 13

```
Lys His Pro Asp Ala Asp Ser Leu Tyr Val Glu Glu Val Asp Val Gly
1               5                   10                  15

Glu
```

<210> SEQ ID NO 14
<211> LENGTH: 17
<212> TYPE: PRT
<213> ORGANISM: Artificial Sequence
<220> FEATURE:
<223> OTHER INFORMATION: synthetic

<400> SEQUENCE: 14

```
Val Leu Lys Arg Leu Glu Gln Lys Gly Ala Glu Ala Asp Gln Ile Ile
1               5                   10                  15

Glu
```

<210> SEQ ID NO 15
<211> LENGTH: 335
<212> TYPE: PRT
<213> ORGANISM: Homo sapiens

<400> SEQUENCE: 15

```
Met Leu Pro Ala Val Ala Val Ser Glu Pro Ser Ser Leu Arg Phe Met
1               5                   10                  15

Ile Phe Cys Arg Leu Leu Ala Lys Met Ala Asn Asn Asp Ala Val Leu
                20                  25                  30

Lys Arg Leu Glu Gln Lys Gly Ala Glu Ala Asp Gln Ile Ile Glu Tyr
            35                  40                  45

Leu Lys Gln Gln Val Ser Leu Leu Lys Glu Lys Ala Ile Leu Gln Ala
        50                  55                  60

Thr Leu Arg Glu Glu Lys Lys Leu Arg Val Glu Asn Ala Lys Leu Lys
65                  70                  75                  80

Lys Glu Ile Glu Glu Leu Lys Gln Glu Leu Ile Gln Ala Glu Ile Gln
                85                  90                  95
```

-continued

```
Asn Gly Val Lys Gln Ile Pro Phe Pro Ser Gly Thr Pro Leu His Ala
            100             105             110
Asn Ser Met Val Ser Glu Asn Val Ile Gln Ser Thr Ala Val Thr Thr
        115             120             125
Val Ser Ser Gly Thr Lys Glu Gln Ile Lys Gly Gly Thr Gly Asp Glu
    130             135             140
Lys Lys Ala Lys Glu Lys Ile Glu Lys Lys Gly Glu Lys Lys Glu Lys
145             150             155             160
Lys Gln Gln Ser Ile Ala Gly Ser Ala Asp Ser Lys Pro Ile Asp Val
            165             170             175
Ser Arg Leu Asp Leu Arg Ile Gly Cys Ile Ile Thr Ala Arg Lys His
        180             185             190
Pro Asp Ala Asp Ser Leu Tyr Val Glu Glu Val Asp Val Gly Glu Ile
    195             200             205
Ala Pro Arg Thr Val Val Ser Gly Leu Val Asn His Val Pro Leu Glu
    210             215             220
Gln Met Gln Asn Arg Met Val Ile Leu Leu Cys Asn Leu Lys Pro Ala
225             230             235             240
Lys Met Arg Gly Val Leu Ser Gln Ala Met Val Met Cys Ala Ser Ser
            245             250             255
Pro Glu Lys Ile Glu Leu Ala Pro Pro Asn Gly Ser Val Pro Gly Asp
            260             265             270
Arg Ile Thr Phe Asp Ala Phe Pro Gly Glu Pro Asp Lys Glu Leu Asn
            275             280             285
Pro Lys Lys Lys Ile Trp Glu Gln Ile Gln Pro Asp Leu His Thr Asn
    290             295             300
Asp Glu Cys Val Ala Thr Tyr Lys Gly Val Pro Phe Glu Val Lys Gly
305             310             315             320
Lys Gly Val Cys Arg Ala Gln Thr Met Ser Asn Ser Gly Ile Lys
            325             330             335
```

METHODS OF DIAGNOSING, TREATING AND MONITORING DIABETIC RETINOPATHY

CROSS-REFERENCE TO RELATED APPLICATIONS

This application represents the national stage entry of PCT International Application No. PCT/US2014/015257 filed on Feb. 7, 2014, which claims the benefit of U.S. Provisional Patent Application Ser. No. 61/763,993 filed on Feb. 13, 2013, the disclosures of which are hereby incorporated by reference in their entirety for all purposes.

FIELD OF THE INVENTION

The invention relates generally to medicine, and more particularly to managing diabetic retinopathy.

BACKGROUND

Diabetic retinopathy (DR) is the most common vascular complication in individuals with long-standing diabetes, with over 7.7 million Americans diagnosed. In the early stages of DR, pericyte loss, basement membrane thickening, and endothelial dysfunction involving loss of endothelial barrier integrity occur. Subsequently, both capillary- and neuro-degeneration result in severe vision defects.

Diabetes causes metabolic and physiologic abnormalities in the retina, and these changes suggest a role for inflammation in the development of DR. Using pharmacologic inhibitors or genetically modified animals, development of at least the early stages of DR, especially occlusion and degeneration of retinal capillaries, has been documented. It is becoming increasingly clear that neuronal cells of the retina also are affected by diabetes, resulting in dysfunction and even degeneration of some neuronal cells.

To date, current strategies for the therapeutic management of DR rely on symptomatic treatments with laser photocoagulation, intravitreal injection of triamcinolone and VEGF-neutralizing agents (e.g., Avastin®), with only partial success and untoward complications (e.g., hemorrhages). There is an enormous need for effective therapies to treat and prevent blindness in individuals suffering from DR, and to monitor the progression of the disease. As such, methods are provided for diagnosing, treating and monitoring DR.

BRIEF SUMMARY

Methods are provided for diagnosing DR in an individual, the method comprising the step of diagnosing the individual as having DR if endothelial monocyte-activating polypeptide II (EMAPII) in a biological sample from the individual is elevated when compared to EMAPII in a control or reference sample. In a preferred embodiment, the biological sample is vitreous humour fluid.

In another aspect, methods are provided for treating an individual having or suspected of having DR comprising the step of administering to the individual a composition comprising a therapeutically effective amount of an agent that inhibits activity or expression of EMAPII. In one embodiment, the agent can be a small molecule inhibitor of EMAPII. In another embodiment, the agent can be a peptide inhibitor of EMAPII. In another embodiment, the agent can be an EMAPII-neutralizing (ENA) antibody (e.g., a humanized M7 monoclonal antibody). In another embodiment, the agent can be a nucleic acid molecule that downregulates EMAPII expression (e.g., siRNA, shRNA or miRNA). In another embodiment, the agent can be an inhibitor of CXCR3 activity or expression. In another embodiment, the individual is pre-determined to have elevated EMAPII in a biological sample, such as vitreous humour fluid.

In another aspect, methods are provided for treating an individual having or suspected of having DR, the method comprising the step of administering to the individual a composition comprising a therapeutically effective amount of an agent that inhibits activity or expression of a CXCR3 receptor. In one embodiment, the agent can be a small molecule inhibitor, especially one selected from the group consisting of AMG487, AT 010 and CXCR3 Antagonist by Zambon Group. In another embodiment, the agent can be a peptide inhibitor of CXCR3. In another embodiment, the agent can be an antibody to CXCR3 (e.g., antibody that inhibits activation of CXCR3). In another embodiment, the agent can be a nucleic acid that down-regulates CXCR3 activity of expression. In another embodiment, the individual is pre-determined to have elevated EMAPII in a biological sample, such as vitreous humour fluid.

In another aspect, methods are provided for monitoring the progression of DR in an individual, the method comprising the step of comparing EMAPII in a first chronological biological sample to a second chronological biological sample from the individual, wherein elevated EMAPII in the second chronological biological sample compared to the first chronological biological sample shows progression of DR. In a preferred embodiment, the biological sample is vitreous humour fluid.

In another aspect, methods are provided for accessing efficacy of a DR treatment in an individual, the method comprising the step of comparing EMAPII from a pre-treatment biological sample from the individual with EMAPII from a post-treatment biological sample from the individual, wherein the treatment is efficacious if EMAPII in the post-treatment sample is attenuated when compared to EMAPII in the pre-treatment biological sample, or wherein the treatment is not efficacious if EMAPII in the post-treatment biological sample is elevated when compared to the pre-treatment biological sample. As such, lower EMAPII post-treatment compared to pre-treatment shows regressing DR.

In another aspect, diagnostic compositions are provided that include a vitreous humour fluid (or a protein extract obtained from a vitreous humor fluid) and one or more exogenous antibodies to EMAPII. In some embodiments the one or more antibodies are covalently or non-covalently linked to a detection agent.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figure 1:
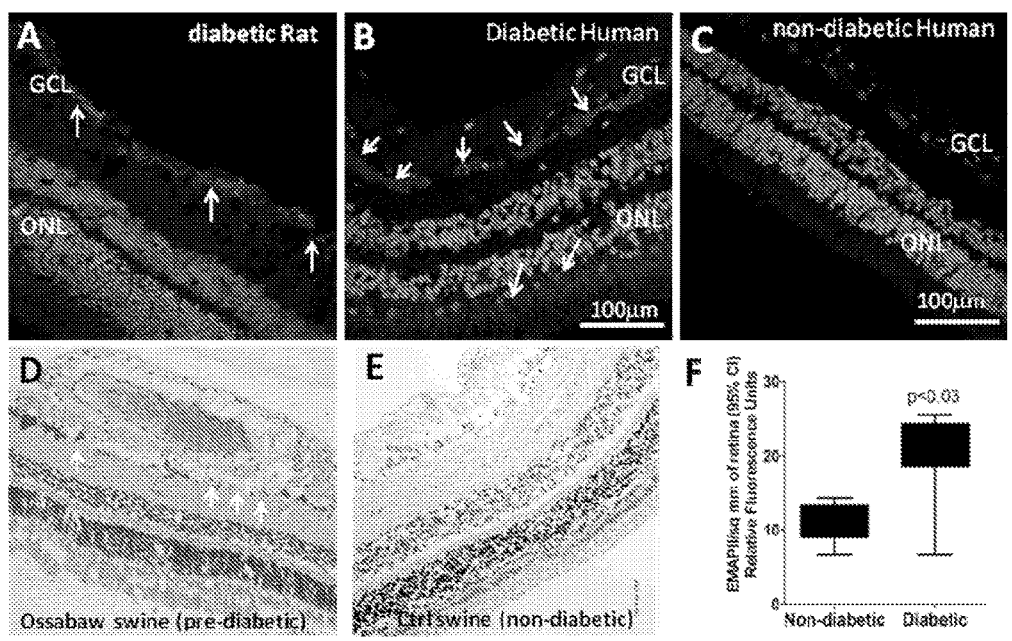
FIG. 1 EMAPII secreted into the vitreous. Immunohistochemical staining with anti-EMAPII from STZ-induced diabetic rat (A), diabetic human (B) and insulin resistant Ossabaw swine (D) demonstrated extensive EMAPII expression (white arrows) within ganglion cell layer (GCL) and outer nuclear layer (ONL) compared to non-diabetic human (C) and swine (E) retina. Data is from a representative experiment from a group size of n=6 (rat), n=3 (ossabaw pig) and n=3 (human). Quantification by MetaMorph analysis for EMAPII in human diabetic retina (F) revealed a 2-3 fold increase in EMAPII compared with non-diabetic human subjects.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

Likewise, many modifications and other embodiments of the present invention set forth herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Overview

Over 7.7 million Americans have been diagnosed with DR, which has no effective treatment that reverses its course or halts its progression. To address these deficiencies, the present disclosure describes methods for diagnosing and treating DR, as well as describes methods of monitoring the status of DR in an individual.

Methods are provided for treating an individual having or suspected of having DR. Briefly, the method comprises administering to the individual a composition comprising a therapeutically effective amount of an agent that inhibits the activity or expression of EMAPII. The agent can be a small molecule or peptide inhibitor of EMAPII, or an EMAPII neutralizing antibody. Alternatively, the agent can be a nucleic acid molecule that down-regulates EMAP II gene expression.

EMAPII (also called endothelial monocyte-activating polypeptide II, EMAP-2, small inducible cytokine subfamily E, member 1 and SCYE1) is a pro-inflammatory protein linked to endothelial response to various forms of cellular stress. EMAPII has been shown to induce endothelial apoptosis and signal through Chemokine Receptor CXCR3 (CXCR3) to cause calcium mobilization and the chemoattraction of endothelial progenitor cells, hematopoietic stem cells, and monocytes. Therefore, methods also are provided for inhibiting EMAPII activity by providing an effective amount of an agent that inhibits the activity or expression of its receptor, CXCR3.

Methods also are provided for monitoring the status of DR in an individual. This method comprises measuring levels of EMAPII from a biological sample from the individual, preferably vitreous humour fluid. This method could be used to diagnose, assess the efficacy of a treatment, and monitor the progression of DR in the individual.

Diabetic Retinopathy

Diabetes mellitus (DM), a representative metabolic disorder caused by long-term maintenance of abnormally high blood glucose (sugar) level, is a systemic, non-contagious chronic disease. DM develops due to an absolutely/relatively diminished production of insulin induced by autoimmune destruction of insulin-producing beta cells of the pancreas or to decreased effects of insulin in a target organ (insulin resistance), which causes a consistent increase of blood glucose level and impairs body metabolism including glucose metabolism.

DR is one of the major microvascular complications of DM, which is caused by inharmonious supply of blood to the retina due to the circulatory disturbance resulting from the gradual deformation and occlusion of the retinal microvessels on account of the consistently high blood glucose level and metabolic abnormality caused thereby. Because the frequency of occurrence of DR increases as the period of suffering from diabetes mellitus is long and there are no warning signs for some time, it is necessary to periodically examine the change of the retina in a diabetic patient.

DR is often divided into two categories for clinical disease management: non-proliferative (or background stage) and a later, proliferative stage. Non-proliferative DR (NPDR) demonstrates, at its outset, abnormalities of the normal microvascular architecture characterized by degeneration of retinal capillaries, formation of saccular capillary microaneurysms, pericyte deficient capillaries, and capillary occlusion and obliteration. Mechanisms of action include diabetes-induced vascular inflammation leading to occlusion of the vascular lumen by leukocytes and platelets followed by the eventual death of both pericytes and endothelial cells. Attraction and adhesion of leukocytes to the vascular wall by the inflammatory process cause leukocytes to adhere temporarily to the endothelium (leukostasis), release cytotoxic factors, and injure or kill the endothelial cell. The damaged endothelial surface initiates platelet adherence, aggregation, microthrombi formation, vascular occlusion and ischemia.

Another consequence of endothelial injury is alteration in the Blood-Retinal Barrier (BRB) causing increased vascular permeability. This can be evidenced by fluorescein leakage during fluorescein angiography or retinal thickening assessed by optical coherence tomography (OCT). Consequences of this leakage can be clinically significant macular edema and deposition of lipoproteins in the retina (hard exudates) contributing to retinal thickening. As the process continues, retinal ganglion cells are lost leading towards visual loss or blindness. The disrupted autoregulation and decreased retinal blood flow resulting from the changes in vasculature in endothelial cells, pericyte death, and capillary obliteration are markers for progression of DR, and leads to development of retinal ischemia, which enables development of the more severe, proliferative stage of DR.

Proliferative DR (PDR) involves neovascularization or angiogenesis, induced by retinal ischemia of the disc or other locations of the retina. This new vasculature can cause hemorrhage of the vitreous humour and retinal detachments from accompanying contractile fibrous tissue. At any point during this progression of DR, macular edema or diabetic macular edema (DME) can develop, with severe impact on vision function. Progression of this associated disorder is predicted by retinal vascular leakage and leads to photocoagulation treatment in order to reduce the risk of vision loss. Since a large proportion of patients with DR suffer from this disorder as well, it is a relevant clinical intervention target. All of these injuries or degenerative insults may lead to impairment or even complete loss of visual acuity and offer targets for therapeutic intervention.

Most often, DR has no symptoms until the eye damage is severe. Symptoms of DR include: blurred vision and gradual vision loss, floaters, shadows or missing areas of vision, and difficulty seeing at nighttime. Many individuals with early DR have no symptoms before major bleeding occurs in the eye. This is why individuals with diabetes should have regular eye exams. In nearly all cases, a health care provider can diagnose DR by dilating the pupils with eye drops and then carefully examining the retina. A retinal photography or fluorescein angiography test may also be used.

No efficient therapeutic options currently are available. Laser photocoagulation involves administering laser burns to various areas of the eye and is used in the treatment of many neovascularization-linked disorders. Neovascularization, in particular, is commonly treated with scatter or panretinal photocoagulation. However, laser treatment may cause permanent blind spots corresponding to the treated areas. Laser treatment may also cause persistent or recurrent hemorrhage, increase the risk of retinal detachment, or induce neovascularization or fibrosis.

Other treatment options for ocular-related disorders include thermotherapy, vitrectomy, photodynamic therapy, radiation therapy, surgery (e.g., removal of excess ocular tissue, and the like). However, in most cases, all available treatment options have limited therapeutic effect, require repeated, costly procedures, and/or are associated with dangerous side effects. Some medications that are used in an off-label manner in the treatment of DR include intravitreal injections of triamcinolone and VEGF antibodies bevacizumab (Avastin®) and ranibuzumab (Lucentis®). These medications can help reduce diabetic macular edema and neovascularization of the disc or retina.

Endothelial Monocyte-Activating Polypeptide II

EMAPII (also called endothelial monocyte-activating polypeptide II, EMAP-2, small inducible cytokine subfamily E, member 1 and SCYE1) was initially discovered as an endothelial- and monocyte-activating polypeptide and later identified as an anti-angiogenic molecule that induces endothelial cell apoptosis. EMAP II is a pro-inflammatory protein that is released from cells as pro- and mature EMAPII proteins in response to various forms of cellular stress, and selectively can induce apoptosis in endothelial cells.

The cDNA encoding EMAPII was cloned in 1994, see, Kao et al., J. Biol. Chem., 269, 9774-9782 (1994), although the polypeptide was identified and purified two years earlier, see, Kao et al., J. Bioi. Chem., 267, 20239-20247 (1992), and the cDNA encoding pro-EMAPII, the precursor of EMAPII, was cloned in 1997, see, Tas et al., Cytokine, 9, 535-539 (1997). Disclosed and claimed in U.S. Pat. No. 6,013,483 is an isolated polynucleotide encoding EMAPII.

EMAPII binds to endothelial cells and leukocytes such as macrophages. EMAPII activates endothelial cells by release of von Willebrand factor, induction of tissue factor, expression of adhesion molecules E-selectin and P-selectin, and elevation of cytosolic free $Ca^{2+}$ concentration, which induces TNF-alpha and tissue factor and stimulates chemotaxis, see, Kao et al., J. Bioi. Chem., 269: 9774-9782 (1994). EMAPII has been shown in mouse embryos to be most abundant at sites of tissue remodeling where many apoptotic cells are detected. The removal of dead cells requires macrophages, which also co-localize with areas of EMAPII expression, see, Knies et al., Proc. Natl. Acad. Sci. U.S.A., 95:12322-12327 (1998).

An inverse correlation between vascularization of the developing lung in fetal mouse and EMAPII expression has been observed, leading to the suggestion that EMAPII is a director of neovascularization since its expression changes spatially during the vascularization process, see, Schwarz et al., Am. J. Physiol. 276: L365-375 (1999). EMAP-II is synthesized as the precursor pro-EMAPII, also called p43, and pro-EMAPII itself is an auxiliary factor of mammalian multi-aminoacyl-tRNA synthetases, see, Quevillon et al. J. Bioi. Chem. 272: 32573-32579 (1997). Pro-EMAPII is also a cytokine but it is secreted from intact mammalian cells, while EMAPII is secreted when cells undergo apoptosis. In vitro, the EMAPII domain is cleaved from pro-EMAPII by caspase 7, see, Shalak et al. J. Biol. Chem. 276: 23769-23776 (2001). As a cytokine, pro-EMAPII triggers proinflammation in leukocytes and macrophages and induces several proinflammatory genes, see, Ko et al., J. Biol. Chem., 276: 23028-23033 (2001). Pro-EMAPII has been proposed to have a role in atherosclerosis development since it is present at high levels in the foam cells of atherosclerotic lesions, see, Ko et al., J. Biol. Chem. 276: 23028-23033 (2001).

As a pro-apoptotic protein, EMAPII may be involved in several disease states. Since EMAPII is a potential mediator of inflammatory responses in autoimmune diseases, EMAPII shows widespread activation in brain lesions of rats with experimental autoimmune encephalomyelitis, neuritis, and uveitis, standard models of rat nervous system autoimmune diseases, see, Schluesener et al., Glia, 20:365-372 (1997). EMAPII is also associated with the development of virus-induced demylinating lesions in rat brain, see, Wege et al., Adv. Exp. Med. Biol., 440: 437-444 (1998). Ischemia followed by reperfusion (I/R) leads to severe organ injury generally as a result of inflammation and apoptosis, another consequence of I/R, contributes to this inflammation. In a mouse model, the presence of apoptosis was directly correlated with posttranslational processing of EMAPII, and thus the prevention of apoptosis in I/R has been suggested as a therapeutic means to treat I/R injury, see, Daemen et al., J. Clin. Invest., 104: 541-549 (1999).

EMAP II can exert its effect on endothelial cells through CXCR3. CXCR3 also is expressed predominantly on T lymphocytes, and also on other lymphocytes (some B cells and NK cells), and is highly induced following cell activation. There are two isoforms—CXCR3-A and CXCR3-B. See, Lasagni et al. J. Exp. Med. 197:1537-1549 (2003). CXCR3 has three highly related ligands in mammals, CXCL9, CXCL10 and CXCL11. See, Tensen et al. J. Invest. Dermatol. 112:716-722 (1999); and Booth et al. Biochemistry 41:10418-10425 (2002). As such, an agent that inhibits activity or expression of EMAPII could be a downregulator of CXCR3 activity or expression.

The genes and protein sequences for EMAP II are known and characterized. See, e.g., GenBank® Accession Nos. AAA62203.1 (mouse) and AAA62202.1 (human); see also, U.S. Pat. Nos. 7,282,208; 7,572,452 and 7,984,426, as well as Kao et al. J. Biol. Chem. 267:20239-20247 (1992); Kao et al. J. Biol. Chem. 269:9774-9782 (1994); and Kao et al. J. Biol. Chem. 269:25106-25119 (1994).

The genes and protein sequences for CXCR3 are known and characterized. See, e.g., GenBank® Accession Nos. NM_001504 (human), NM_009910 (mouse), and NM_053415 (rat).

Inhibitors of EMAPII and CXCR3

Inhibition of EMAPII or CXCR3 activity could be used for the treatment of DR. Preferably, the inhibitor of EMAPII or CXCR3 function is a compound that is, for example, a small organic molecule, natural product, protein (e.g., antibody, chemokine, cytokine), peptide or peptidomimetic. Molecules that can inhibit EMAPII that are known in the art are inhibitory peptides that bind to EMAPII and block its activity, such as Z-ASTD-FMK, sold by Biovision. Z-ASTD-FMK is a synthetic peptide that reversibly inhibits EMAPII activity released during apoptosis.

Several molecules that can inhibit one or more functions of chemokine receptors (e.g., CXCR3) are known in the art, as reviewed in Collins et. al. Chemokine Biology, Basic Research and Clinical Applications, Vol III (2007), including the small organic molecules disclosed in, for example, international patent application WO 97/24325 by Takeda Chemical Industries, Ltd.; WO 98/38167 by Pfizer, Inc.; WO 97/44329 by Teijin Limited; WO 98/04554 by Banyu Pharmaceutical Co., Ltd.; WO 98/27815, WO 98/25604, WO 98/25605, WO98/25617 and WO 98/31364 by Merck & Co., Inc.; Hesselgesser et al., J. Biol. Chem. 273(25):15687-15692 (1998); Axten et al. US 2005/0272936; Kawada et al. 2009/0208486; Anilkumar et al. U.S. Pat. No. 7,868,005 and Howard et al., J. Medicinal Chem. 41(13):2184-2193 (1998); proteins, such as antibodies (e.g., polyclonal sera, monoclonal, chimeric, humanized, human) and antigen-binding fragments thereof (e.g., Fab, Fab', F(ab') 2, Fv), for example, those disclosed in WO 98/11218 by Theodor-Kocher Institute and LeukoSite, Inc.; chemokine mutants and analogues, for example, those disclosed in U.S. Pat. No. 5,739,103 issued to Rollins et al., WO 96/38559 by Dana Farber Cancer Institute, US 2002/0039578, US 2005/0112119, U.S. Pat. No. 7,405,275, US 2010/0047238, and WO 98/06751 by Research Corporation Technologies, Inc.; peptides, for example, those disclosed in WO 98/09642 by The United States of America.

In some embodiments the agent that inhibits the activity of CXCR3 is selected from a group consisting of AMG487, AT 010, and CXCR3 Antagonists ZAMBON. AMG487 is described in Tonn et al. Drug Metab Dispo 37:502-13 (2008). AT 010 is a CXCR3 antagonist being developed for cancer and inflammatory disorders by Affitech NS. CXCR3 Antagonist ZAMBON is being co-developed for inflammatory disorders by Zambon Company SpA, Cosmo Pharmaceuticals SpA, and BioXell SpA.

As used herein, "treat," "treating" and the like means a slowing, stopping or reversing of progression of a disease or disorder characterized by DR in an individual when provided EMAPII inhibitor or a CXCR3 inhibitor. As such, "treating" means an application or administration of a EMAPII inhibitor or CXCR3 inhibitor, or the application or administration of a pharmaceutical composition comprising an EMAPII or CXCR3 antibody, where the individual has a disease or a symptom of a disease, where the purpose is to cure, heal, alleviate, relieve, alter, remedy, ameliorate, improve or affect the disease or symptoms of the disease.

As used herein, "inhibit," "inhibiting" and the like means that expression, activity or function of a target biological activity, e.g., EMAPII or its cognate receptor, CXCR3, can be decreased in cells or an individual by a statistically significant amount including, but not limited to, about 5%, 10%, 15%, 20%, 25%, 30%, 35%, 40%, 45%, 50%, 55%, 60%, 65%, 70%, 75%, 80%, 85%, 90%, 95% or 100% when contacted with an inhibitor as described herein.

As used herein, "pharmaceutically acceptable" or "pharmacologically acceptable" means a material which is not biologically or otherwise undesirable, i.e., the material may be administered to an individual in a formulation or composition without causing any undesirable biological effects or interacting in a deleterious manner with any of the components of the composition in which it is contained.

The pharmaceutical compositions of this invention can be administered by a variety of routes, as described in, e.g., Edelhauser et al (2010), *Investigative Opthalmology & Visual Science,* 51(11):5403-5420. Such methods include, by way of non-limiting examples, topical instillation of ophthalmic drops, intravitreal, intra ocular, oral, transdermal, subcutaneous, intravenous, intramuscular and intranasal. Depending upon the intended route of delivery, the pharmaceutical composition preferably is formulated as either injectable or sustained drug release systems or oral compositions or as salves, as lotions or as patches all for transdermal administration. The preferred method of administration is intravitreal injection.

The compositions for oral administration can take the form of bulk liquid solutions or suspensions, or bulk powders. More commonly, however, the compositions are presented in unit dosage forms to facilitate accurate dosing. As used herein, "unit dosage forms" means a physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the combination therapy is usually a minor component (from about 0.1% to about 50% by weight or preferably from about 1% to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions typically are based upon injectable sterile saline or phosphate-buffered saline or other injectable carriers known in the art. As before, the active compound in such compositions is typically a minor component, often being from about 0.05% to 10% by weight with the remainder being the injectable carrier and the like.

Transdermal compositions are typically formulated as a topical ointment or cream containing the active ingredient(s), generally in an amount ranging from about 0.01% to about 20% by weight, preferably from about 0.1% to about 20% by weight, preferably from about 0.1 to about 10% by weight, and more preferably from about 0.5% to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well known in the art and generally include additional ingredients to enhance the dermal penetration of stability of the active ingredients or the formulation. All such known transdermal formulations and ingredients are included within the scope of this invention.

The pharmaceutical composition also can be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th ed., 1985, Mack Publishing Company, Easton, Pa.

The pharmaceutical compositions also can be administered in sustained release forms or from sustained release drug delivery systems. A description of representative sustained release materials can be found in *Remington's Pharmaceutical Sciences,* supra.

The following formulation examples illustrate representative pharmaceutical compositions that may be prepared in accordance with this invention. The present invention, however, is not limited to the following pharmaceutical compositions.

Formulation 1—Tablets:

A pharmaceutical composition may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules:

A pharmaceutical composition may be admixed as a dry powder with a starch diluent in an approximate 1:1 weight ratio. The mixture is filled into 250 mg capsules (125 mg of active compound per capsule).

Formulation 3—Liquid:

A pharmaceutical composition (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets:

A pharmaceutical composition may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection:

A pharmaceutical composition may be dissolved or suspended in a buffered sterile saline injectable aqueous medium to a concentration of approximately 5 mg/mL.

Formulation 6—Topical:

Stearyl alcohol (250 g) and a white petrolatum (250 g) may be melted at about 75° C. and then a mixture of a pharmaceutical composition (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

The pharmaceutical composition can be administered as therapeutic agents to an individual having or suspected of having DR or related disease.

One of skill in the art would appreciate that the choice as to which composition or compositions of the invention are well suited to a particular application must take into consideration such variables as the severity of the disease or condition, mode of administration, and duration of administration.

Antibodies

In some embodiments of the methods disclosed herein is a method of treating a diabetic neuropathy in a patient, comprising providing one or more EMAPII neutralizing antibodies. These antibodies can prevent EMAPII from binding to its receptor (e.g. CXCR3), and/or inhibit the activity of EMAPII. For example see Clauss et. al. (WO 2012/170929 and WO 2009/117680), which describe a rat M7 clone that binds to EMAPII and has been shown to be useful in diagnosing and treating lung disease and injury, and Schwarz (U.S. Pat. No. 7,264,803), which describes a pharmaceutical formulation for treating pulmonary hypertension comprising a humanized antibody to EMAPII.

In some embodiments, the antibodies to be used in the methods described herein are humanized antibodies. In other embodiments the antibodies to be used are or non-humanized antibodies. In some embodiments, the antibodies to be used comprise: a heavy chain variable region that includes at least a portion of the amino acid sequence of SEQ. ID. NO. 2 (see Table 1); and a light chain variable region, wherein said light chain variable region includes at least a portion of a second polypeptide according to SEQ. ID. NO. 3, wherein the antibodies bind to at least one form of EMAPII. In some embodiments the first polypeptide has at least 99 percent homology to SEQ. ID. NO. 2, and said second polypeptide has at least 99 percent homology to SEQ. ID. NO. 3. In other embodiments, the first polypeptide has at least 95 percent identity to SEQ. ID. NO. 2, and said second polypeptide has at least 95 percent identity to SEQ. ID. NO. 3. In other embodiments the first polypeptide has at least 99 percent identity to SEQ. ID. NO. 2, and said second polypeptide has at least 99 percent identity to SEQ. ID. NO. 3. And in still other embodiments, the first polypeptide is SEQ. ID. NO. 2, and said second polypeptide is SEQ. ID. NO. 3. In some embodiments the antibodies bind to at least the pro form of EMAPII (pro-EMAPII), and in some embodiments the antibodies bind to EMAPII found in humans and/or in mice and/or in other mammals.

In some embodiments, an antibody to be used comprises: a heavy chain, wherein CDRI includes at least a portion of the amino acid sequence of SEQ. ID. NO. 5, CDR2 includes at least a portion of the polypeptide according to SEQ. ID. NO. 6, and CDR3 includes at least a portion of the polypeptide according to SEQ. ID. NO. 7; and a light chain, wherein said light chain includes the light chain hypervariable regions CDRI L CDR2 L, and CDR3 L, wherein CDRIL includes at least a portion of the polypeptide according to SEQ. ID. NO. 8, CDR2 L includes at least a portion of the polypeptide according to SEQ. ID. NO. 9 and CDR3 L includes at least a portion of the polypeptide according to SEQ. ID. NO. 10. In some embodiments, the antibody comprises a heavy chain wherein CDRI H, CDR2 H, and CDR3 H correspond to amino acid sequences of SEQ ID NOs: 5-7, respectively, with up to three conservative amino acid changes in each of the CDR H sequences. In some embodiments, the antibody comprises a light chain wherein CDRI L, CDR2 L, and CDR3 L correspond to amino acid sequences of SEQ ID NOs: 8-10, respectively, with up to three conservative amino acid changes in each of the CDR L. In some embodiments, CDR1 is SEQ. ID. NO. 5, CDR2 is SEQ. ID. NO. 6, and CDR3 is SEQ. ID. NO. 7; and CDRI L is SEQ. ID. NO. 8, CDR2 L is SEQ. ID. NO. 9, and CDR3 L is SEQ. ID. NO. 10.

In some embodiments, the aforementioned CDR sequences are utilized in a humanized antibody, that binds to human EMAPII. In some embodiments the antibodies bind to at least the pro form of EMAPII (pro-EMAPII), and in some embodiments the antibodies bind to EMAPII found in humans and/or in mice and/or in other mammals. In some embodiments the antibodies are humanized.

In some embodiments, the antibodies to be used in the methods described herein bind to an epitope of human EMAP II, wherein the epitope includes at least a portion of an isolated polypeptide according to SEQ. ID. NO. 12. In some embodiments, the isolated polypeptide comprises an amino acid at least 95 percent identity to SEQ. ID. NO. 12 (e.g., 96%, 97%, 98%, 99%, or 100% identical). In some embodiments the the amino acid sequence of the isolated polypeptide consists of SEQ ID NO:12. In other embodiments, the isolated polypeptide comprises an amino acid sequence at least 95% identical to SEQ. ID. NO. 11 (e.g., 96%, 97%, 98%, 99%, or 100% identical). In some embodiments, the amino acid sequence of the isolated polypeptide consists of SEQ. ID. NO. 11.

TABLE 1

Antibody and EMAP II Epitope Sequences

| SEQ. ID. NO. 1 | GCGGTGCACCTTGTTGAGTCTGGTGGAGGATTTGT GCAGCCTACGGAGTCATTGAAAATCTCATGTGCA GCCTCTGGATTCACCTTCAGTGATGCTGCCATGTA CTGGGTCCGCCAGGCTCCAGGAAAGGGTCTGGAA TGGGTTGCTCGCATAAGAACTAAACCTAATAATT ATGCCACATATTATGCTGATTCAGTGAAAGGCAG ATTCACCATCTCCCGAGATGATTCAAAAAGCATG GTCTACCTACAAATGGATAACTTGAAAACTGAGG ACACAGCCATGTATTACTGTACATCATGGAGCTA CGACTTTGATTACTGGGGCCAAGGAGTCATGGTC ACAGTCTCCTCA | Nucleotide sequence of the IgG heavy chain from rat antibody hybridoma clone M7/1. |

TABLE 1 -continued

Antibody and EMAP II Epitope Sequences

| | | |
|---|---|---|
| SEQ. ID. NO. 2 | AVHLVESGGGFVQPTESLKISCAASGFTFSDAAMY WVRQAPGKGLEWVARIRTKPNNYATYYADSVKGR FTISRDDSKSMVYLQMDNLKTEDTAMYYCTSWSY DFDYWGQGVMVTVSS | Polypeptide sequence of the IgG heavy chain from rat antibody hybridoma clone M7/1. |
| SEQ. ID. NO. 3 | DIVMTQGALPNPVPSGESASITCQSSKSLLHSSGKTY LNWYLQRPGQSPHLLIYQMSTRASGVSDRLSGSGS GTDFTLKISSVEAEDVGVYYCQQFLEYPLTFGSGTK LEIK | Polypeptide sequence of the IgG heavy chain from rat antibody hybridoma clone M7/1. |
| SEQ. ID. NO. 4 | GATATTGTGATGACCCAGGGTGCACTCCCCAACC CTGTCCCCTCTGGAGAGTCAGCTTCCATCACCTGC CAGTCTAGTAAGAGTCTGCTGCACAGCAGTGGCA AGACATACTTGCAATTGGTATCTGCAGAGGCCAGG ACAGTCTCCTCATCTCCTGATCTATTGGATGTCCA CCCGTGCATCAGGAGTCTCAGACAGGCTCAGTGG CAGTGGGTCAGGAACAGATTTCACACTGAAAATC AGCAGCGTGGAGGCTGAGGATGTGGGTGTGTATT ACTGTCAGCAATTTCTAGAGTATCCTCTCACGTTC GGTTCTGGGACCAAGCTGGAGATCAAAC | Nucleotide sequence of the IgG light chain from rat antibody hybridoma clone M7/1. |
| SEQ. ID. NO. 5 | GFTFSDAA | Polypeptide CDR1 from IgG heavy chain of rat antibody hybridoma clone M7/1. |
| SEQ. ID. NO. 6 | IRTKPNNYAT | Polypeptide CDR2 from IgG heavy chain of rat antibody hybridoma clone M7/1. |
| SEQ. ID. NO. 7 | TSWSYDFDY | Polypeptide CDR3 from IgG heavy chain of rat antibody hybridoma clone M7/1. |
| SEQ. ID. NO. 8 | KSLLHSSGKTY | Polypeptide CDR1 from IgG light chain of rat antibody hybridoma clone M7/1. |
| SEQ. ID. NO. 9 | WMS | Polypeptide CDR2 from IgG light chain of rat antibody hybridoma clone M7/1. |
| SEQ. ID. NO. 10 | QQFLEYPLT | Polypeptide CDR3 from IgG light chain of rat antibody hybridoma clone M7/1. |
| SEQ. ID. NO. 11 | QQSIAGSADSKPIDVSRLDRIGCIITARKHPDADSLY VEEVDVGEIAPRTVVSGLVNHVPLEQMQNRM | Polypeptide sequence identified in human EMAPII as the portion of the protien that is protected from trypsin digestion by the binding of rat antibody hybridoma clone M7/1. |
| SEQ. ID. NO. 12 | QQSIAGSADSKPIDVSR | Polypeptide sequnece from human EMAPII that interacts with rat antibody hybridoma clone M7/1. |

TABLE 1 -continued

Antibody and EMAP II Epitope Sequences

SEQ. ID. NO. 13 KHPDADSLYVEEVDVGE
Polypeptide sequnece from human EMAPII that does not appear to interact strongly with rat antibody hybridoma clone M7/1.

SEQ. ID. NO. 14 VLKRLEQKGAEADQIIE
Random, synthetic polypeptide sequence that does not interact with rat antibody hybridoma clone M7/1.

SEQ. ID. NO. 15 MLPAVAVSEPSSLRFMIFCRLLAKMANNDAVLKRL
EQKGAEADQIIEYLKQQVSLLKEKAILQATLREEKK
LRVENAKLKKEIEELKQELIQAEIQNGVKQIPFPSGT
PLHANSMVSENVIQSTAVTTVSSGTKEQIKGGTGDE
KKAKEKIEKKGEKKEKKQQSIAGSADSKPIDVSRLD
LRIGCIITARKHPDADSLYVEEVDVGEIAPRTVVSGL
VNHVPLEQMQNRMVILLCNLKPAKMRGVLSQAMV
MCASSPEKIELAPPNGSVPGDRITFDAFPGEPDKELN
PKKKIWEQIQPDLHTNDECVATYKGVPFEVKGKGV
CRAQTMSNSGIK
Polypeptide sequence of human EMAPII.

In an alternate embodiment, antibodies that bind to CXCR3 and inhibits ligand binding to the receptor and/or its activity could also be used to treat DR in a patient, for example, see Kassam et. al. (US 2005/0112119); Qin et. al. (U.S. Pat. No. 7,405,275); and Kanakaraj et. al (US 2010/0047238), which describe human CXCR3 antibodies.

As used herein, "antibody" or "antibodies" includes an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). For example, the term includes bivalent or bispecific molecules, diabodies, triabodies and tetrabodies. Bivalent and bispecific molecules are described in, e.g., Kostelny et al. J Immunol 148:1547 (1992); Pack & Pluckthun Biochemistry 31:1579 (1992); Zhu et al. Protein Sci. 6:781 (1997); Hu et al. Cancer Res. 56:3055 (1996); Adams et al. (1993) Cancer Res. 53:4026 (1993); and McCartney et al. (1995) Protein Eng. 8:301 (1995). The term "antibody" also includes antigen binding forms of antibodies, including fragments with antigen-binding capability (e.g., Fab', F(ab')$_2$, Fab, Fv and rIgG). The term also refers to recombinant single chain Fv fragments (scFv). In some embodiments, antibodies employed to practice the present invention bind to its target protein with a $K_D$ value of equal to or greater affinity than $10^7$ M$^{-1}$, e.g., $10^8$ M$^{-1}$, $10^9$ M$^{-1}$, $10^{10}$ M$^{-1}$, $10^{11}$ M$^{-1}$, or $10^{12}$ M$^{-1}$, As used herein, an "antibody" means a monoclonal and polyclonal antibody and can belong to any antibody class (i.e., IgG, IgM, IgA, etc.). One of ordinary skill in the art is familiar with methods for making monoclonal antibodies (Mab). For example, one of ordinary skill in the art can make monoclonal antibodies by isolating lymphocytes and fusing them with myeloma cells, thereby producing hybridomas. See, e.g., Milstein C, "Handbook of experimental immunology," (Blackwell Scientific Pub., 1986); and Goding J, "Monoclonal antibodies: principles and practice," (Academic Press, 1983), each of which is incorporated herein by reference as if set forth in its entirety. The cloned hybridomas are then screened for production of, for example, "anti-EMAPII" or "anti-CXCR3" (i.e., antibodies that bind preferentially to EMAPII or CXCR3 or fragments thereof). Monoclonal antibodies are thus not limited by the manner in which the antibodies are produced, whether such production is in situ or not. Alternatively, antibodies can be produced by recombinant DNA technology including, but not limited to, expression in bacteria, yeast, insect cell lines or mammalian cell lines. These antibodies can be chimeric antibodies or humanized antibodies to be useful for the treatment of humans.

Likewise, one of ordinary skill in the art is familiar with methods of making polyclonal antibodies. For example, one of ordinary skill in the art can make polyclonal antibodies by immunizing a suitable host animal such as, for example, a rabbit, with an immunogen and using properly diluted serum or isolating immunoglobulins from the serum. The animal may therefore be inoculated with the immunogen, with blood subsequently being removed from the animal and an IgG fraction purified. Other suitable host animals include a chicken, goat, sheep, guinea pig, rat or mouse. If desired, the immunogen may be administered as a conjugate in which the immunogen is coupled, for example, via a side chain of one of its amino acid residues, to a suitable carrier. The carrier molecule is typically a physiologically acceptable carrier. The antibody obtained may be purified to a purity of up to about 70%, up to about 80%, up to about 90%, up to about 95%, up to about 99% or up to about 100%.

Antibody also encompasses functional fragments, like Fab and F(ab') 2, of anti-EMAPII or anti-CXCR3. Treatment of antibodies with proteolytic enzymes, such as papain and pepsin, generates these antibody fragments, especially anti-EMAPII and anti-CXCR3.

Antibodies are typically conjugated to a detectable label for easy visualization. Examples of suitable labels for the methods and kits described herein include, but are not limited to, radiolabels, biotin (which may be detected by avidin or streptavidin conjugated to peroxidase), lanthanides, alkaline phosphatase and fluorescent labels (e.g., fluorescein, rhodamine, especially the Alexa Fluor® family of fluorescent dyes available from Invitrogen/Molecular Probes). Labelling of the antibody can be carried out by, e.g.

labeling free amine groups (covalently or non-covalently). Some labels can be detected by using a labeled counter suitable for the detection of the label in question.

As used herein, the phrase "human antibody" refers to an antibody or an antigen-binding fragment of an antibody in which the variable and constant regions (if present) have amino acid sequences that are encoded by nucleotide sequences derived from human (*Homo sapiens*) germ line immunoglobulin genes. A "human antibody" can include sequences that are not encoded in the germ line (e.g., due to N nucleotides, P nucleotides, and mutations that can occur as part of the processes that produce high-affinity antibodies such as, somatic mutation, affinity maturation, clonal selection) that occur as a result of biological processes in a suitable in vivo expression system (e.g., a human, a human-antibody transgenic animal). Antibodies, antigen-binding fragments of antibodies and portions or regions of human antibodies can be produced, for example, by expression of a nucleic acid of non-human origin (e.g., a synthetic nucleic acid) that has the requisite nucleotide sequence.

As used herein, "humanized antibody" refers to an antibody or antigen-binding fragment thereof comprising a CDR that is not of human origin and framework and/or constant regions that are of human origin. For example, a humanized antibody can comprise a CDR derived from an antibody of nonhuman origin (e.g., natural antibody such as a murine (e.g., mouse, rat) antibody, artificial antibody) that binds a human EMAPII or human CXCR3, and framework and constant regions (if present) of human origin (e.g., a human framework region, a human consensus framework region, a human constant region (e.g., CL, CHI, hinge, CH2, CH3, CH4)). CDR-grafted single chain antibodies containing a CDR of non-human origin and framework and constant regions (if present) of human origin (e.g., CDR-grafted scFV) are also encompassed by the term humanized antibody.

As used herein, the term "chimeric antibody" refers to an antibody or antigen-binding fragment thereof comprising a variable region from an antibody from a first species and a constant region from an antibody from a different species. None of the portions which comprise a chimeric antibody needs to be of human origin. For example, a chimeric antibody can comprise a variable region from a rodent (e.g., mouse) antibody and a constant region of a non-human primate antibody (e.g., a chimpanzee constant region).

The EMAPII or CXCR3 antibody can be a single chain antibody (e.g., a single chain Fv (scFv)) and can include a linker moiety (e.g., a linker peptide) not found in native antibodies. For example, a scFv can comprise a linker peptide, such as two to about twenty glycine residues or other suitable linker, which connects a heavy chain variable region to a light chain variable region. For the purposes of the application, the presence of such a linker does not affect the status of the single chain antibody as being "of human origin" or "human." For example, a human scFv can comprise a human heavy chain variable region and a human light chain variable region which are connected through a suitable peptide linker.

Nucleic Acid Inhibition of Gene Expression.

Inhibition of EMAPII activity can be achieved by inhibition of EMAPII gene expression, for example, see Bennett et. al (US 2004/0110144), which describes a compound comprising a nucleic acid molecule encoding EMAPII, wherein the compound specifically hybridizes with said nucleic acid molecule encoding EMAPII. Alternatively, inhibition of EMAPII activity can be achieved by inhibition of CXCR3 gene expression, for example see Taketo et. al. (US 2009/0208486).

The present application provides methods that include targeted delivery of inhibitor nucleic acids. One such method is through RNA interference, particularly short interfering RNA (siRNA) molecules or micro RNA molecules (miRNA) into cells both in vitro and in vivo. These methods are useful, for example, in treatment of diseases, wherein cell specific gene silencing is desired.

RNA interference (RNAi) is a mechanism of posttranscriptional gene silencing (PTGS) that has been described in plants, invertebrates, and mammalian cells (Sharp *P. A. Nature Struct. Biol.* 8:746-750 (2001); Bernstein et al. *Nature* 409:363-366; Hannon (2002) *Nature* 418:244-251 (2001). In mammals, exposure to shorter than about 30 base pairs (bp) long short interference RNA (siRNA) molecules leads to mRNA degradation with specificity to the target RNA (Elbashir et al. *Genes Dev.* 15:188-200 (2001); Elbashir et al. *EMBO J.* 20:6877-6888 (2001).

The advantage of RNAi lies in its high specificity and potent gene silencing, coupled with the fact that every gene is a potential target and every cell has the necessary machinery. Although some questions remain about specificity and activation of off-target effects, none of these problems has yet been documented in vivo. Moreover, some potential untoward events can likely be avoided by judicious choice of sequences or chemical modification of siRNAs.

The RNA interference-inducing molecule according to the present invention includes RNA molecules that have natural or modified nucleotides, natural ribose sugars or modified sugars and natural or modified phosphate backbone. Accordingly, the RNA interference-inducing molecule referred to in the specification includes, but is not limited to, unmodified and modified double stranded (ds) RNA molecules including, short-temporal RNA (stRNA), small interfering RNA (sRNA), short-hairpin RNA (shRNA), microRNA (miRNA), double-stranded RNA (dsRNA), (see, e.g., Baulcombe, *Science* 297:2002-2003 (2002)). The dsRNA molecules, e.g. sRNA, also may contain 3' overhangs, preferably 3'UU or 3'TT overhangs. In one embodiment, the sRNA molecules of the present invention do not include RNA molecules that comprise ssRNA greater than about 30-40 bases, about 40-50 bases, about 50 bases or more. In one embodiment, the sRNA molecules of the present invention have a double stranded structure. In one embodiment, the sRNA molecules of the present invention are double stranded for more than about 25%, more than about 50%, more than about 60%, more than about 70%, more than about 80%, more than about 90% of their length.

As used herein, "polynucleotide" or "gene" means a polymer of nucleic acids or nucleotides. Although it may comprise any type of nucleotide units, the term generally applies to nucleic acid polymers of ribonucleotides ("RNA") or deoxyribonucleotides ("DNA"). The term is used to include single-stranded nucleic acids, double-stranded nucleic acids, and RNA and DNA made from nucleotide or nucleoside analogues that may be identified by their nucleic acid sequences, which are generally presented in the 5' to 3' direction (as the coding strand), where the 5' and 3' indicate the linkages formed between the 5' hydroxyl group of one nucleotide and the 3'-hydroxyl group of the next nucleotide. For a coding strand presented in the 5'-3' direction, its complement (or non-coding strand) is the strand that hybridizes to that sequence according to Watson-Crick base pairing. Thus, as used herein, the complement of a nucleic acid is the same as the "reverse complement" and describes the nucleic acid that in its natural form, would be based paired with the nucleic acid in question.

As used herein, a "nucleic acid" sequence means a DNA or RNA sequence. The term encompasses sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

A "vector" is a replicon, such as a plasmid, phage, or cosmid, to which another nucleic acid segment may be attached so as to bring about the replication of the attached segment. A vector is capable of transferring gene sequences to target cells (e.g., bacterial plasmid vectors, particulate carriers and liposomes).

Typically, the terms "vector construct," "expression vector," "gene expression vector," "gene delivery vector," "gene transfer vector," and "expression cassette" all refer to an assembly which is capable of directing the expression of a sequence or gene of interest. Thus, the terms include cloning and expression vehicles.

As used herein, "isolated polynucleotide" or "isolated polypeptide" means a polynucleotide or polypeptide isolated from its natural environment or prepared using synthetic methods such as those known to one of ordinary skill in the art. Complete purification is not required in either case. The polynucleotides and polypeptides described herein can be isolated and purified from normally associated material in conventional ways, such that in the purified preparation the polynucleotide or polypeptide is the predominant species in the preparation. At the very least, the degree of purification is such that extraneous material in the preparation does not interfere with use of the polynucleotide or polypeptide in the manner disclosed herein. The polynucleotide or polypeptide is at least about 85% pure; alternatively, at least about 95% pure; and alternatively, at least about 99% pure.

Further, an isolated polynucleotide has a structure that is not identical to that of any naturally occurring nucleic acid molecule or to that of any fragment of a naturally occurring genomic nucleic acid spanning more than one gene. An isolated polynucleotide also includes, without limitation, (a) a nucleic acid having a sequence of a naturally occurring genomic or extrachromosomal nucleic acid molecule, but which is not flanked by the coding sequences that flank the sequence in its natural position; (b) a nucleic acid incorporated into a vector or into a prokaryote or eukaryote host cell's genome such that the resulting polynucleotide is not identical to any naturally occurring vector or genomic DNA; (c) a separate molecule such as a cDNA, a genomic fragment, a fragment produced by polymerase chain reaction (PCR) or a restriction fragment; and (d) a recombinant nucleotide sequence that is part of a hybrid gene (i.e., a gene encoding a fusion protein). Specifically excluded from this definition are nucleic acids present in mixtures of clones, e.g., as these occur in a DNA library such as a cDNA or genomic DNA library. An isolated polynucleotide can be modified or unmodified DNA or RNA, whether fully or partially single-stranded or double-stranded or even triple-stranded. In addition, an isolated polynucleotide can be chemically or enzymatically modified and can include so-called non-standard bases such as inosine.

As used herein, "polypeptide," "peptide" and "protein" are used interchangeably herein to mean a polymer of amino acids. The terms apply to amino acid polymers in which one or more amino acid residues is an artificial chemical analogue of a corresponding naturally occurring amino acid, as well as to naturally occurring amino acid polymers.

Standard techniques may be used for recombinant DNA, oligonucleotide synthesis, and tissue culture and transformation (e.g., electroporation, lipofection, etc.). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout. See, e.g., Sambrook et al. Molecular Cloning: A Laboratory Manual (2d ed., Cold Spring Harbor Laboratory Press, Cold Spring Harbor, N.Y. (1989)).

Methods of Monitoring the Status of DR.

We have demonstrated that EMAPII is expressed in diabetic rat, pig and human retina, and that EMAPII expression is induced in human retinal endothelial cells following hyperglycemia. Another aspect of the present application is a method of monitoring the progression of DR in an individual by comparing the levels of EMAPII in the individual. An individual could be diagnosed as having DR if they have elevated EMAPII levels in a biological sample from the individual, compared to a control or reference sample, the biological sample preferably vitreous humour fluid. The progression of DR in a patient can be monitored by comparing levels of EMAPII from the individual of a first chronological sample with a second chronological sample Alternatively, the efficacy of a therapeutic treatment for DR could also be monitored by comparing the levels of EMAPII from a biological sample from the individual pre-treatment to the levels of EMAPII in a biological sample from the individual post-treatment. Reduced expression of EMAPII would show improvement of the disease, or show an effective therapy. Increased expression of EMAPII would show worsening of the disease or lack of efficacy of the therapy.

In some embodiments encompassed herein are diagnostic compositions comprising one or more exogenous antibodies to EMAPII (as described herein) and a vitreous humor fluid. In other embodiments, the compositions comprise one or more exogenous antibodies to EMAPII and a crude protein extract or protein fraction obtained from a vitreous humour fluid. Protein extraction from vitreous humour fluid is known in the art as described in, e.g., Angi et al (2012), *Mediators of Inflammation*; Vol. 2012; Article ID 148039. In some embodiments, the one or more antibodies are linked, covalently or non-covalently, to a detection agent, as described herein.

As used herein, the term "biological sample" is used herein in its broadest sense. A biological sample may be obtained from an individual (e.g., a human) or from components (e.g., tissues) of an individual. The sample may be of any biological tissue or fluid with which EMAPII may be assayed. Frequently, the sample will be a "clinical sample", i.e., a sample derived from a patient. Such samples include, but are not limited to, bodily fluids, e.g., urine, blood, blood plasma, vitreous humour fluid, saliva; tissue or fine needle biopsy samples; and archival samples with known diagnosis, treatment and/or outcome history. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of, filtration, distillation, extraction, concentration, inactivation of interfering components, addition of reagents, and the like. In a preferred embodiment, the biological sample is vitreous humour fluid.

The biological samples used in the practice of the methods may be fresh or frozen samples collected from an individual, or archival samples with known diagnosis, treatment and/or outcome history. Biological samples may be collected by any non-invasive means, such as, for example, by collecting an individual's vitreous humour fluid. In certain aspects, the inventive methods are performed on the biological sample itself without or with limited processing of the sample.

As used herein, the term "control sample" or "reference sample" refers to one or more biological samples isolated from an individual or group of individuals that are normal (i.e., healthy). The term "control sample" (or "control") can also refer to the compilation of data derived from samples of one or more individuals classified as normal, or one or more individuals diagnosed with diabetes.

Preferably, there is enough of the biological sample to accurately and reliably determine the abundance of EMAPII. Multiple biological samples may be taken from the individual in order to obtain a representative sampling from the individual.

In still other embodiments, the methods are performed on a protein extract prepared from the biological sample. Preferably, the protein extract contains the total protein content. However, the methods may also be performed on extracts containing one or more of: membrane proteins, nuclear proteins, and cytosolic proteins. Methods of protein extraction are well known in the art, see, for example "Protein Methods", D. M. Bollag et al., 2nd Ed., (1996), Wiley-Liss; "Protein Purification Methods: A Practical ApprIPSch", E. L. Harris and S. Angal (Eds.), (1989); "Protein Purification Techniques: A Practical Approach", S. Roe, 2nd Ed., (2001), Oxford University Press; "Principles and Reactions o/Protein Extraction, Purification, and Characterization", H. Ahmed, (2005), CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kits most appropriate for a particular situation. After the protein extract has been obtained, the protein concentration of the extract is preferably standardized to a value being the same as that of the control sample in order to allow signals of the protein markers to be quantitated. Such standardization can be made using photometric or spectrometric methods or gel electrophoresis.

In yet other aspects, the methods are performed on nucleic acid molecules extracted from the biological sample. For example, RNA may be extracted from the sample before analysis. Methods of RNA extraction are well known in the art, see, for example, J. Sambrook et al., "Molecular Cloning: A Laboratory Manual", (1989), 2nd Ed., Cold Spring Harbor Laboratory Press: Cold Spring Harbor, N.Y. Most methods of RNA isolation from bodily fluids or tissues are based on the disruption of the tissue in the presence of protein denaturants to quickly and effectively inactivate RNAses. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain aspects, after extraction, mRNA is amplified, and transcribed into cDNA, which can then serve as template for multiple rounds of transcription by the appropriate RNA polymerase. Amplification methods, e.g., real time qPCR, are well known in the art, see, for example, A. R. Kimmel and S. L. Berger, Methods Enzymol. (1987), 152: 307-316; J. Sambrook et al., "Molecular Cloning: A Laboratory Manual", (1989), 2nd Ed., Cold Spring Harbour Laboratory Press: New York; "Short Protocols in Molecular Biology", F. M. Ausubel (Ed.), (2002), 5th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

The methods of the present application generally involve the determination of the abundance levels of EMAPII polypeptides in a biological sample obtained from an individual. Determination of protein levels may be performed by any suitable method, see, for example, E. Harlow and A. Lane, "Antibodies: A Laboratories Manual", (1988), Cold Spring Harbor Laboratory: Cold Spring Harbor, N.Y.

In general, EMAPII protein levels can be determined by contacting a biological sample isolated from an individual with binding agents for EMAPII, in the sample, the levels of polypeptides that bind to the binding agents; and comparing the levels of polypeptides in the sample with the levels of polypeptides in a control sample. As used herein, the term "binding agent" refers to an entity such as a polypeptide or antibody that specifically binds to an inventive protein marker. An entity "specifically binds" to a polypeptide if it reacts/interacts at a detectable level with the polypeptide but does not react/interact detectably with peptides containing unrelated sequences or sequences of different polypeptides.

In other aspects, the binding agent is an antibody specific for EMAPII. Suitable antibodies for use in the methods of the present invention include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods of the application can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration.

Instead of being prepared, antibodies to be used in the methods of the present invention may be obtained from scientific or commercial sources.

In certain embodiments, the binding agent is directly or indirectly labeled with a detectable moiety. The role of a detectable agent is to facilitate the detection step of the diagnostic method by allowing visualization of the complex formed by binding of the binding agent to the protein marker (or analog or fragment thereof). Preferably, the detectable agent is selected such that it generates a signal which can be measured and whose intensity is related (preferably proportional) to the amount of protein marker present in the sample being analyzed. Methods for labeling biological molecules such as polypeptides and antibodies are well known in the art, see, for example, "Affinity Techniques. Enzyme Purification. Part B", Methods in Enzymol., (1974), Vol. 34, W. B. Jakoby and M. Wilneck (Eds.), Academic Press: New York, N.Y.; and M. Wilchek and E. A. Bayer, Anal. Biochem., 171: 1-32 (1988).

Any of a wide variety of detectable agents can be used to detect EMAPII expression. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain aspects, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Protein levels in the methods of the present application may be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well known in the art. As will be appreciated by one skilled in the art, the immunoassay may be competitive or noncompetitive. Methods of detection and quantification of the signal generated by the complex formed by binding of the binding agent with the protein marker will depend on the nature of the assay and of the detectable moiety (e.g., fluorescent moiety).

Alternatively, the protein levels may be determined using mass spectrometry based methods or image (including use of labeled ligand) based methods known in the art for the detection of proteins. Other suitable methods include proteomics-based methods. Proteomics, which studies the global changes of protein expression in a sample, typically includes the following steps: (1) separation of individual proteins in a sample by electrophoresis (I-D PAGE), (2) identification of individual proteins recovered from the gel (e.g., by mass spectrometry or N-terminal sequencing), and (3) analysis of the data using bioinformatics.

As already mentioned above, the methods for quantifying levels of EMAPII may involve determination of the expression levels of a set of nucleic acid molecules comprising polynucleotide sequences coding for an inventive protein marker. Determination of expression levels of nucleic acid molecules in the practice of the inventive methods may be performed by any suitable method, including, but not limited to, Southern analysis, Northern analysis, polymerase chain reaction (PCR), see, for example, U.S. Pat. Nos. 4,683,195; 4,683,202, and 6,040,166; "PCR Protocols: A Guide to Methods and Applications", Innis et al. (Eds.) (1990), Academic Press: New York), reverse transcriptase PCR(RT-PCT), anchored PCR, competitive PC, see, for example, U.S. Pat. No. 5,747,251, rapid amplification of cDNA ends (RACE), see, for example, "Gene Cloning and Analysis: Current Innovations, (1997), pp. 99-115; ligase chain reaction (LCR) (see, for example, EP 01 320308, one-sided PCR, see, for example Ohara et al., Proc. Natl. Acad. Sci., 86: 5673-5677 (1989), in situ hybridization, Taqman based assays, see for example Holland et al., Proc. Natl. Acad. Sci., 88:7276-7280 (1991), differential display, see, for example, Liang et al., Nucl. Acid. Res., 21: 3269-3275 (1993) and other RNA fingerprinting techniques, nucleic acid sequence based amplification (NASBA) and other transcription based amplification systems, see, for example, U.S. Pat. Nos. 5,409,818 and 5,554,527, Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of polynucleotide sequences in biological samples may be constructed using conventional methods known in the art. Suitable probes may be based on nucleic acid sequences encoding at least 5 sequential amino acids from regions of nucleic acids encoding a protein marker, and preferably comprise about 15 to about 50 nucleotides. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well known in the art (for a review of labeling protocols, label detection techniques and recent developments in the field, see, for example, L. J. Kricka, Ann Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes may be used in hybridization techniques to detect polynucleotides encoding the protein markers. The technique generally involves contacting an incubating nucleic acid molecules in a biological sample obtained from an individual with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for a protein marker may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Hybridization and amplification techniques described herein may be used to assay qualitative and quantitative aspects of expression of nucleic acid molecules comprising polynucleotide sequences coding for the inventive protein markers.

Alternatively, oligonucleotides or longer fragments derived from nucleic acids encoding each protein marker may be used as targets in a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; Chen et al., Genomics, 1998, 51: 313324; U.S. Pat. Nos. 5,143,854; 5,445,934; 5,807,522; 5,837,832; 6,040,138; 6,045,996; 6,284,460; and 6,607,885).

Once the levels of EMAPII has been determined for the biological sample being analyzed, they are compared to the levels in one or more control samples or to at least one known DR patient. Comparison of levels according to methods of the present application is preferably performed after the levels obtained have been corrected for both differences in the amount of sample assayed and variability in the quality of the sample used (e.g., amount of protein extracted, or amount and quality of mRNA tested). Correction may be carried out using different methods well known in the art. For example, the protein concentration of a sample may be standardized using photometric or spectrometric methods or gel electrophoresis (as already mentioned above) before the sample is analyzed. In case of samples containing nucleic acid molecules, correction may be carried out by normalizing the levels against reference genes (e.g., housekeeping genes) in the same sample. Alternatively or additionally, normalization can be based on the mean or median signal (e.g., Ct in the case of RT-PCR) of all assayed genes or a large subset thereof (global normalization approach).

Using methods described herein, skilled physicians may select and prescribe treatments to a patient that expresses elevated EMAPII levels, in particular an agent that inhibits EMAPII activity or expression. In particular, the present invention provides physicians with a non-subjective means to diagnose DR, which will allow for early treatment, when intervention is likely to have its greatest effect. Monitoring the expression levels of EMAPII over the course of the treatment can indicate whether the therapy is effective or not. Reduced levels of EMAP II over time or following a treatment is indicative of improved disease state.

EXAMPLES

The invention will be more fully understood upon consideration of the following non-limiting examples, which are offered for purposes of illustration, not limitation.

Example 1: EMAPII is Expressed in the Retinas of Rat, Ossabaw Pig, and Human with Diabetic Retinopathy To determine the cellular localization of EMAPII in the retina, we examined six streptozotocin-induced diabetic athymic rat retinas after 2 months of diabetes. As shown in FIG. 1, EMAPII is produced in the ganglion cell layer (GCL) and more so in diabetic rat retinas compared to non-diabetic rat retinas. Furthermore, this same observation was seen in a pre-diabetic, insulin resistant, and high fat fed Ossabaw pig but not control pig. More interestingly, human retina with DR was highly positive for EMAPII expression (23.9±0.9, n=3) v/s non-diabetic controls (13.7±0.6, n=2, MetaMorph analysis, blinded investigator) specifically in GCL as well as around blood vessels and photoreceptors.

Example 2: MAPII is Secreted and Measurable in the Diabetic Vitreous

Figure 2:
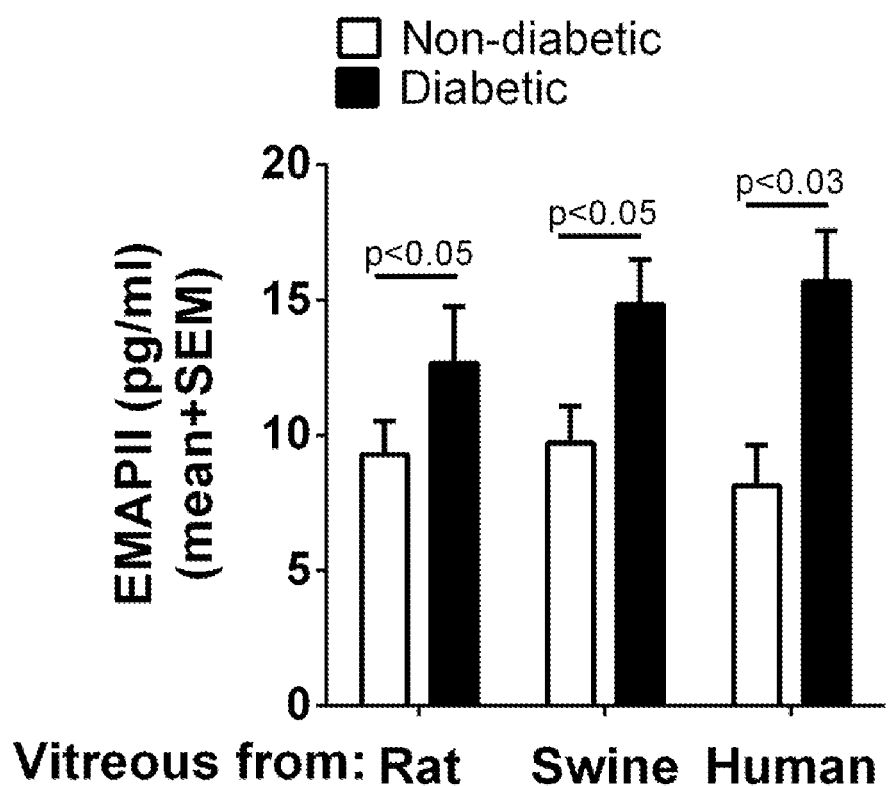
FIG. 2 EMAPII secreted into the vitreous. A commercially available ELISA analysis revealed a 2-3 fold increase in EMAPII levels in the diabetic vitreous compared with non-diabetic subjects. Data is from a group size of 3-4

Although EMAPII was identified as a component of the macromolecular aminoacyl tRNA synthetase complex involved in the cellular translation process, it has also been found to be secreted as a cytokine having complex physiological functions. Secreted EMAPII was measured using a commercially available ELISA kit (Antigenix America, RHF902CKX) in vitreous samples from diabetic human subjects, diabetic rats and diabetic swine. As shown in FIG. 2, diabetic vitreous EMAPII levels were about 2-3 fold higher compared to non-diabetic controls. Although more studies are warranted, the increased levels of EMAPII could be correlated with severity of DR.

Figure 3:
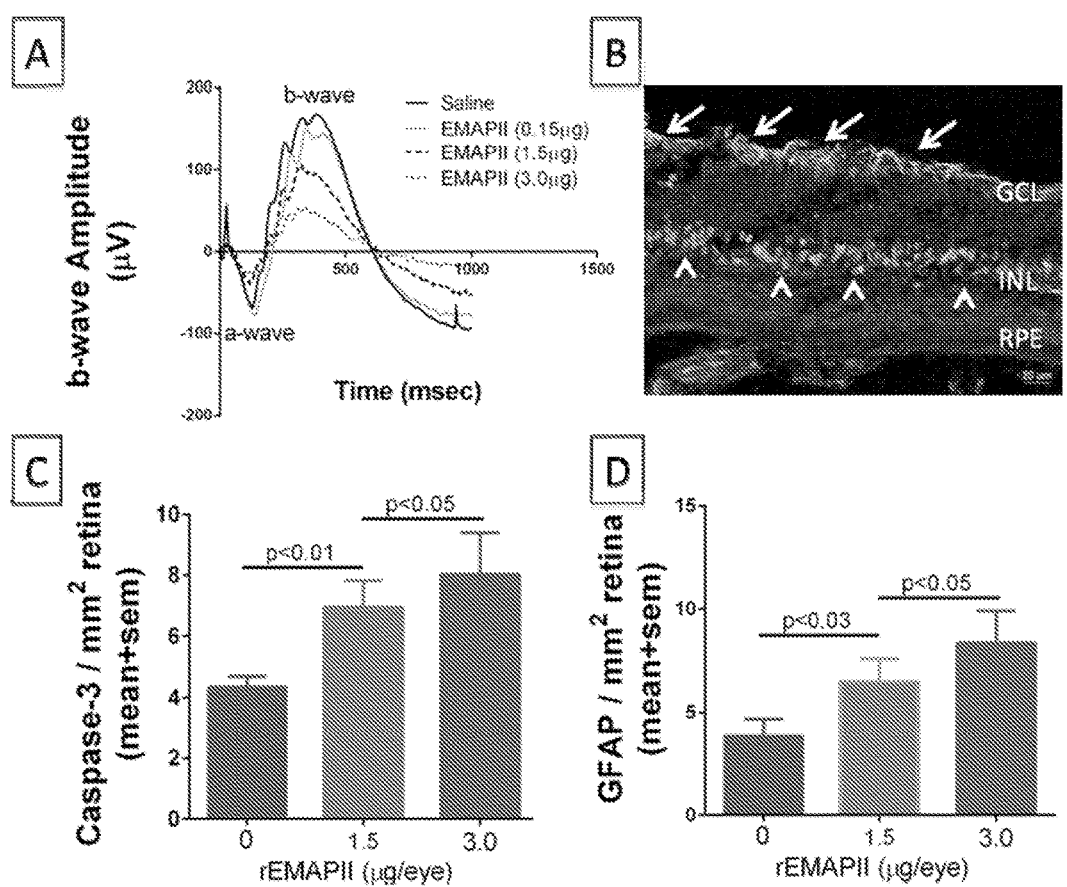
FIG. 3 Intravitreal EMAPII damage in the retina. (A). A dose dependent decrease in b-wave amplitudes is noted with intravitreal recombinant human EMAPII into Lewis rat eyes after 7-days. (B). Enucleated eyes embedded in tissue-tek, cut at 7 μm and stained with anti-Caspase-3 (9661, cell Signaling; arrow heads) and anti-GFAP (ab7260, Abcam; arrows) demonstrated extensive immunostaining within the retina. MetaMorph quantification of signal intensities at day-7 revealed a dose dependent increase in apoptosis (C) and gliosis (D). Data is from a group size of 3-4 animals.

Example 3: Intravitreal Injection of EMAPII in Non-Diabetic Rats and Retinal Pathology To determine if intravitreal injection of EMAPII damage retina, we used a recombinant human EMAPII (Sino Biologicals) at increasing dose (0.15-3.0 µg/eye) and injected intravitreally into one eye of Lewis rats with other eye serving as a control with equal volume of saline injection. At day 7 post injection, electroretinography performed on dark-adapted rats clearly demonstrated a dose-dependent decrease in b-wave amplitude in rats that received EMAPII compared to those received saline injection (FIG. 3A). This is accompanied by an increase in both gliosis as evidenced by GFAP immunostaining and apoptosis as evidenced by active-caspase-3 immunostaining in these rats (FIGS. 3B-D).

Figure 4:
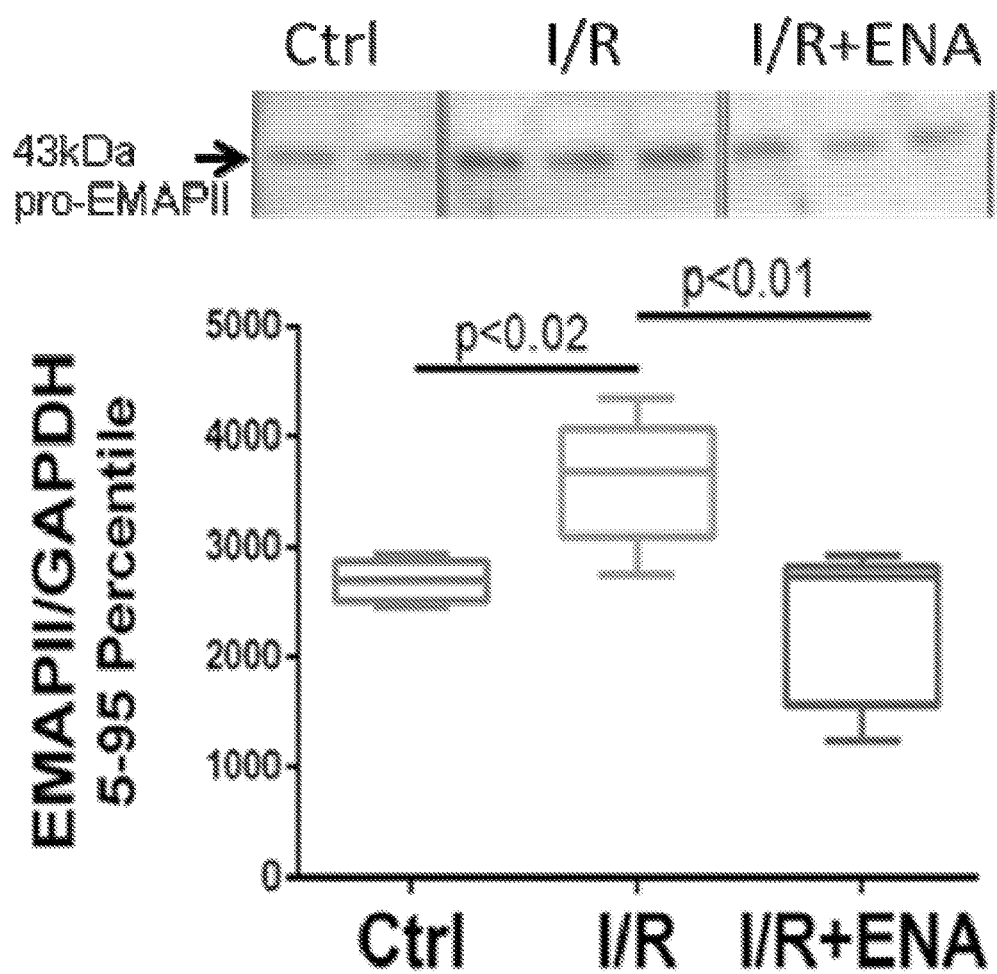
FIG. 4 EMAPII is elevated in retinal I/R injury. Western blot analysis with anti-EMAPII antibody in retinal extracts demonstrated a >2 fold increase in EMAPII in injured (I/R) eyes compared to uninjured (control) eyes. Furthermore, pre-treatment with ENA (I/R+ENA) decreased EMAPII levels to control levels. Data is from a group size of 3-4 animals.
Figure 5:
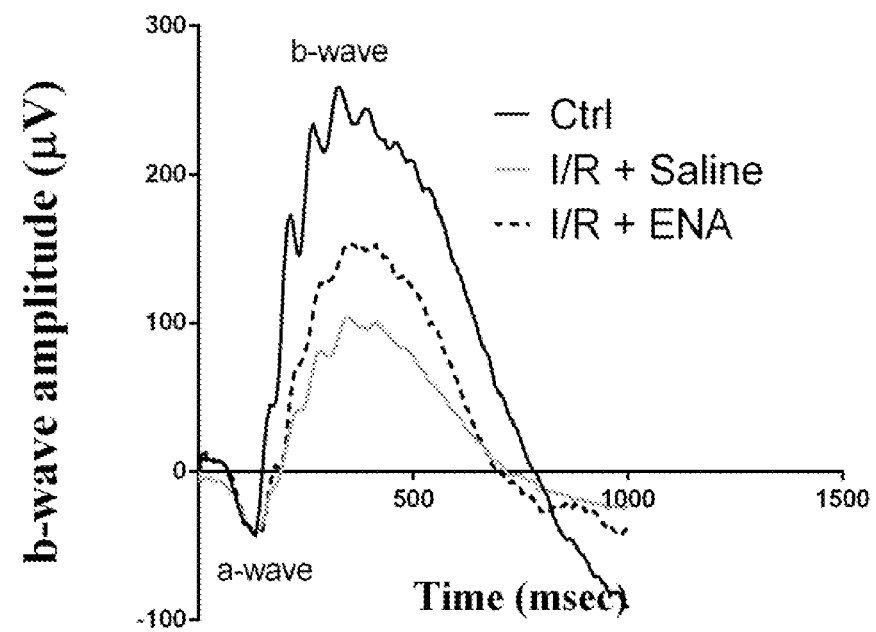
FIG. 5 Intravitreal injection of neutralizing antibody to EMAPII rescues retinal I/R injury. About 30 minutes prior to I/R injury intravitreal injection of ENA significantly rescued b-wave response. Data is from a group size of 3-4 animals.
Figure 5:
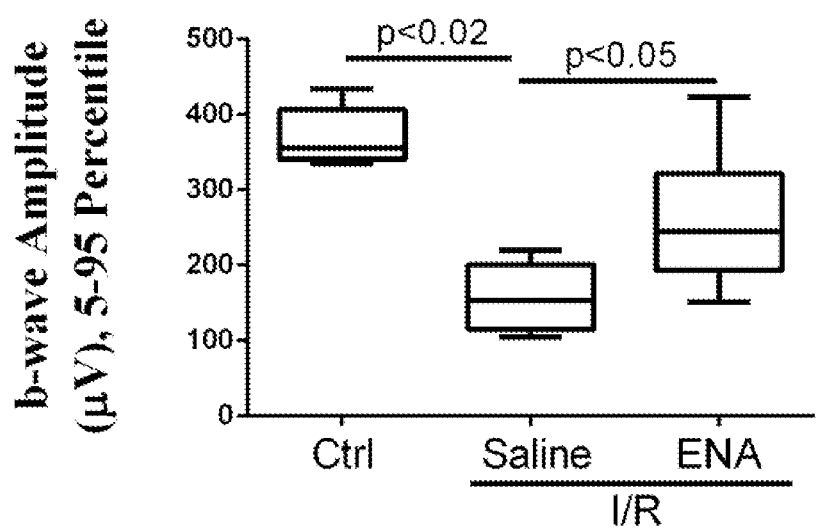

Example 4: Intravitreal Injection of Neutralizing Antibody to EMAPII Rescues Retinal Damage in I/R Injury Rats Subsequent to gain of function in the above study with intravitreal recombinant EMAPII, we performed loss of function experiments. Previously, we have shown a neutralizing antibody to EMAPII raised in rats blocked endothelial apoptosis in vitro and protected against cigarette smoke-induced pulmonary emphysema. In light of these impressive data, we then tested this EMAPII neutralizing antibody (ENA) in our retinal I/R injury model. As shown in the FIG. 5 ERG data analyzed at day 7 demonstrated a significant decrease in the b-wave response in I/R injured eyes compared to un-injured eyes which can be correlated with 2-3 fold increase in EMAPII levels observed in injured eyes. Intravitreal injection of ENA (15 µg/ml final concentration assuming vitreous volume 56±4 µL; 2 µL injection) about 30 minutes prior to I/R injury significantly alleviated this decrease in b-wave response, suggesting a therapeutic role for ENA in retinal degeneration. Furthermore, Western blot analysis of retinal extracts from ENA injected eyes significantly decreased EMAPII levels compared to injured eyes with saline confirming that the observed effects on b-wave are indeed due to EMAPII (FIG. 4).

Example 5: High glucose (HG) Induces EMAPII Expression in Human Retinal Endothelial Cells (HREC)

Figure 6:
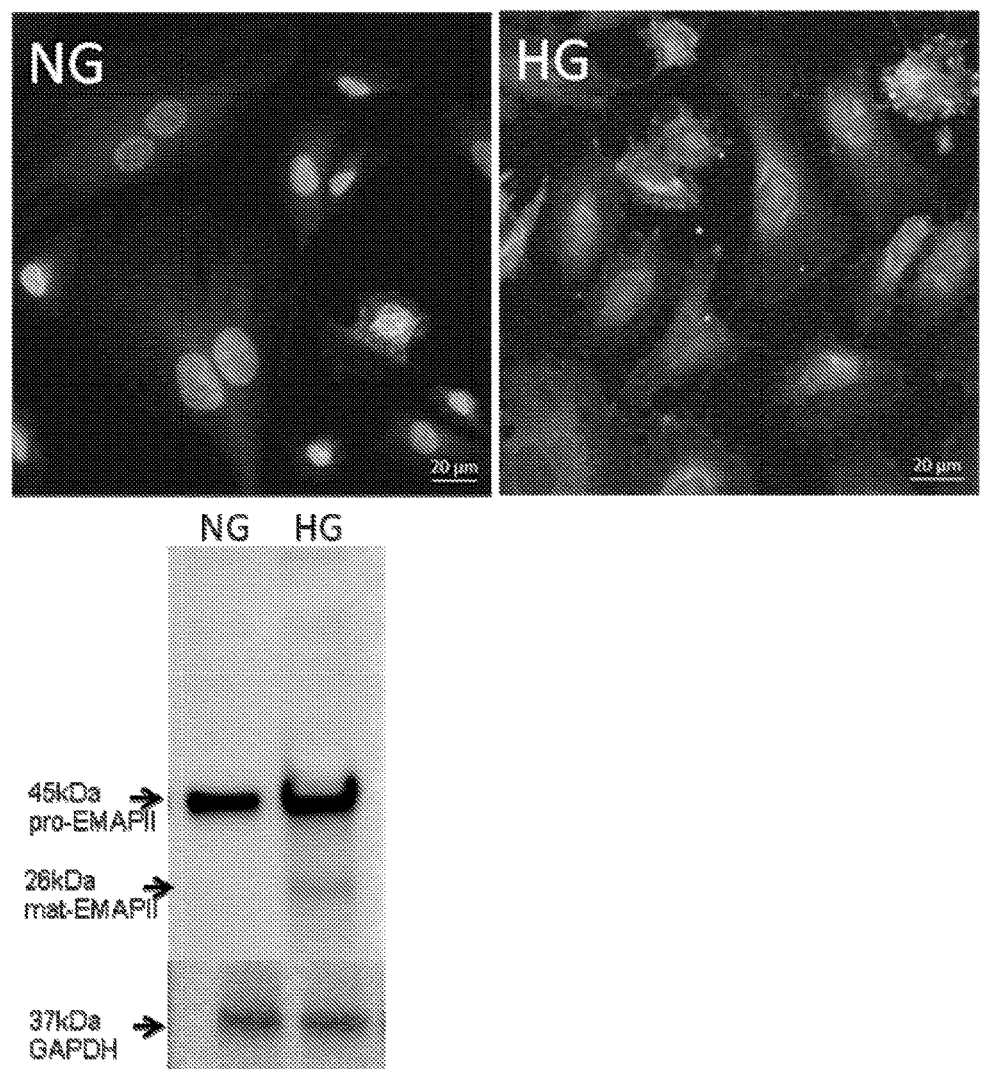
FIG. 6 Hyperglycemia induces EMAPII expression in HREC. About $1\times10^5$ human retinal endothelial cells (HREC) were cultured under high glucose conditions (HG; 25 mM D-Glucose) with daily media change for 7 days. Cells were fixed with ice cold methanol for immunocytochemistry for EMAPII or prepared total cell lysates for Western blot. As shown in hyperglycemic conditions (top right panel) extensive cytoplasmic EMAPII was noted compared to HREC cultured in normoglycemia (NG; 5.5 mM D-Glucose) which was further confirmed by Western blot (left bottom panel). Interestingly, HG conditions also revealed a 26 kDa mature EMAPII. Data is from a representative experiment performed in duplicates and repeated 3 additional times independently.

As diabetes is a chronic low grade inflammatory disease, we first tested the hypothesis that HREC subjected to acute and chronic doses of HG will induce EMAPII. HREC were subjected to 25 mM glucose for 24 hrs or chronically treated every 24 hrs with 25 mM glucose for 7 days and assessed EMAPII expression by confocal microscopy. A marked increase in cytoplasmic EMAPII was noted with acute HG in 24 h (not shown) which was further increased in chronically treated HREC (FIG. 6) suggesting that EMAPII is induced by HG. Moreover, HG conditions also revealed a 26 kDa mature EMAPII by Western blot suggesting both pro and mature forms of EMAPII may be involved in hyperglycemia.

Example 6: HG Induced EMAPII Expression is Time- and Dose-Dependent

Figure 7:
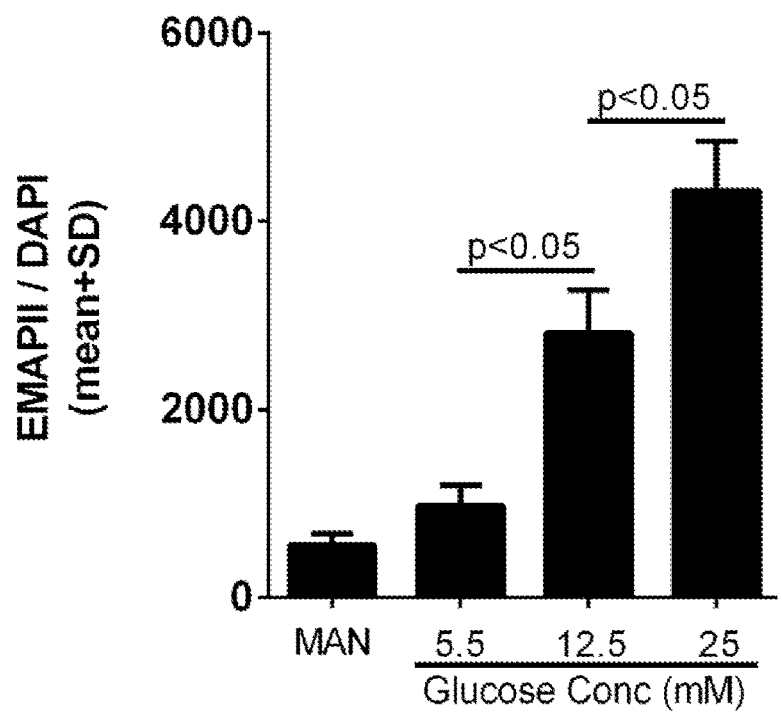
FIG. 7 Expression of EMAPII under hyperglycemic condition is dose and time-dependent. A significant ($p<0.01$) increase in EMAPII levels noted as early as 6 hrs with a 2-3 fold increase in 12.5 mM glucose compared to normal glucose concentrations. Data is from a representative experiment performed in triplicates and repeated one more time with similar results.
Figure 7:
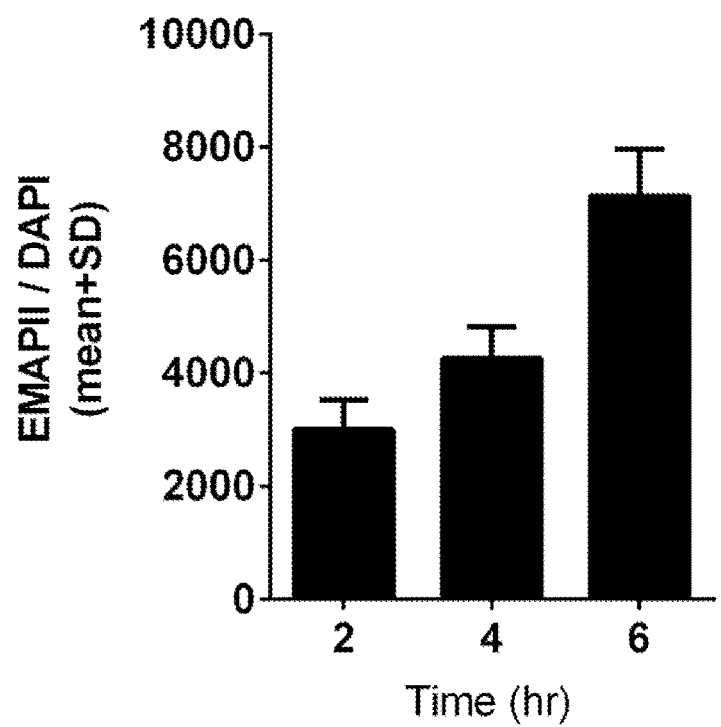

In this study we wanted to establish if EMAPII exhibited a dose- and time-dependent expression with HG. To this end, HREC were subjected to increasing doses of HG or mannitol (as osmotic control) for 6 hrs or used a fixed 25 mM glucose levels to assess a time dependent increase in EMAPII. As shown in FIG. 7, it is interesting to note that the increased EMAPII expression in HREC acutely with HG is both dose and time dependent suggesting that EMAPII is dynamically changed in HG conditions. Furthermore, this increase in EMAPII with HG is not evident in 25 mM mannose treated wells (FIG. 7, upper panel) which rules out glucose mediated osmotic effects.

Example 7: HG Induced Apoptosis in HREC is Mediated by EMAPII

Figure 8:
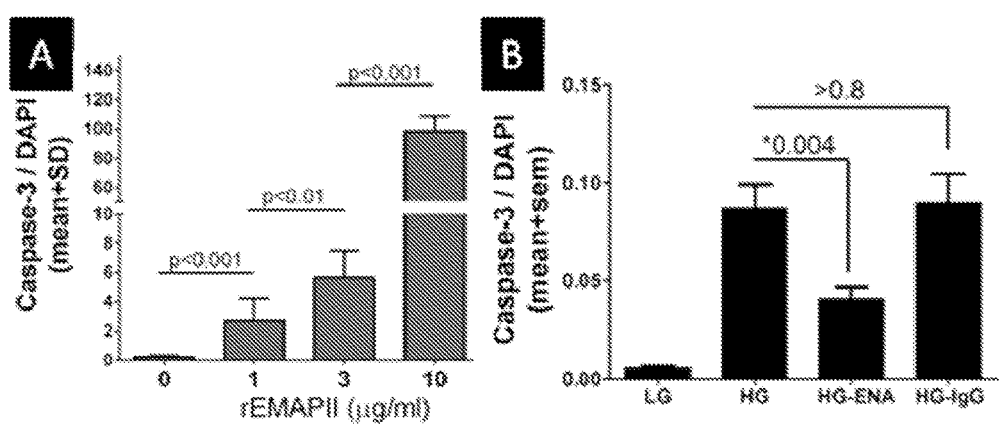
FIG. 8 Neutralizing antibody to EMAPII rescues HREC from high glucose induced apoptosis. (A). EMAPII in a dose dependent fashion increase HREC apoptosis. (B). HG induced apoptosis compared to LG is rescued by pre-treatment with ENA but not with an isotype control (HG-IgG). Data is from a representative experiment performed in triplicates and repeated one more time with similar results.

Previously we have shown that EMAPII induces apoptosis in lung endothelial cells In this study, we tested if EMAPII induced apoptosis in HREC. To this end, HREC were subjected to increasing doses of EMAPII and assessed proliferation and apoptosis. EMAPII dose dependently decreased proliferation (Ki67 assay, data not shown) with a concurrent increase in apoptosis evidenced by capase-3 (FIG. 8).

Because we know that HG induces apoptosis in HREC we wanted to identify if EMAPII played a key role in the observed increase in apoptosis with HG in HREC. To this end, HREC were treated with 25 mM glucose with and without 10 ng/ml EMAPII neutralizing antibody (ENA) or IgG isotype control. HG-induced apoptosis was significantly down-regulated with ENA (FIG. 8) but not with isotype control antibodies, suggesting a central role for EMAPII in HG conditions. As a positive control, in a parallel experiment recombinant human EMAPII was added to HREC to confirm that EMAPII does induce apoptosis in HREC as we have noted previously with human lung microvascular endothelial cells (HLMVEC) (FIG. 8).

Figure 9:
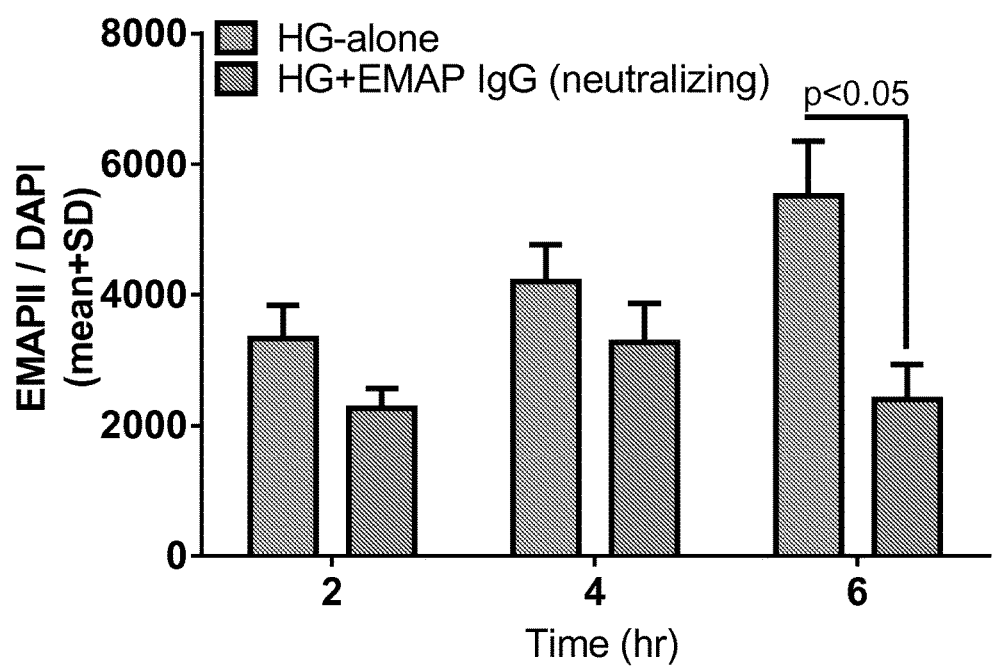
FIG. 9. shows plots illustrating the levels of EMAPII antigen in response to hyperglycemic conditions HREC cells in the presence or absence of an EMAPII antibody.

Example 8: EMAP II Neutralizing Ab (ENA) Decreases Time Dependent Increase in EMAP II Under Hyperglycemia Human retinal endothelial cells (HREC) challenged with 25 mM Glucose for either 2, 4 or 6 hrs with or without EMAP neutralizing antibody (ENA). Immunostaining of HREC for EMAPII antigen demonstrated a dose dependent increase in EMAPII under hyperglycemic conditions which could be blocked with pre-incubation with ENA (FIG. 9).

Figure 10:
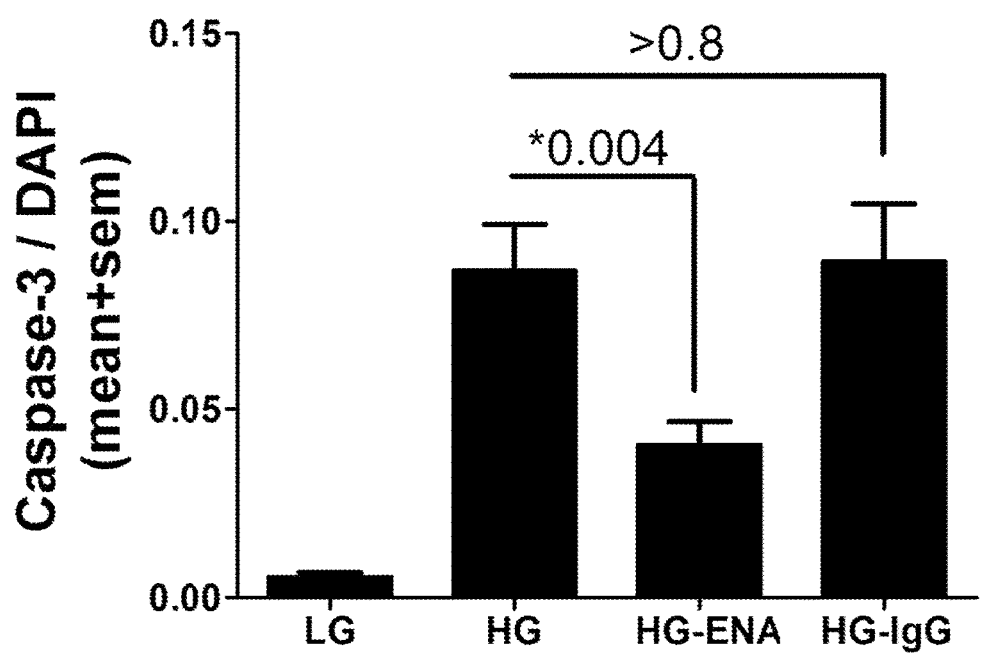
FIG. 10. shows plots illustrating the level of caspase 3 staining (as an indicator of apoptosis) in human retinal endothelial cells (HREC) cells under hyperglycemic or normal glucose conditions for 24 hrs in the presence or absence of an EMAP neutralizing antibody (ENA).

Example 9: EMAP II Neutralizing Ab (ENA) Decreases Hyperglycemia Induced Apoptosis Human retinal endothelial cells (HREC) challenged with 25 mM Glucose for 24 hr with or without EMAP neutralizing antibody (ENA). Immunostaining of HREC for active Caspase-3 antigen demonstrated a significant increase in apoptosis under hyperglycemic conditions (HG) compared with normal glucose conditions (LG). Interestingly, pre-incubation with ENA but not rat IgG abrogated the apoptosis as evidenced from decreased Caspase-3 only in HREC that were challenged with HG+ENA (FIG. 10).

Figure 11:
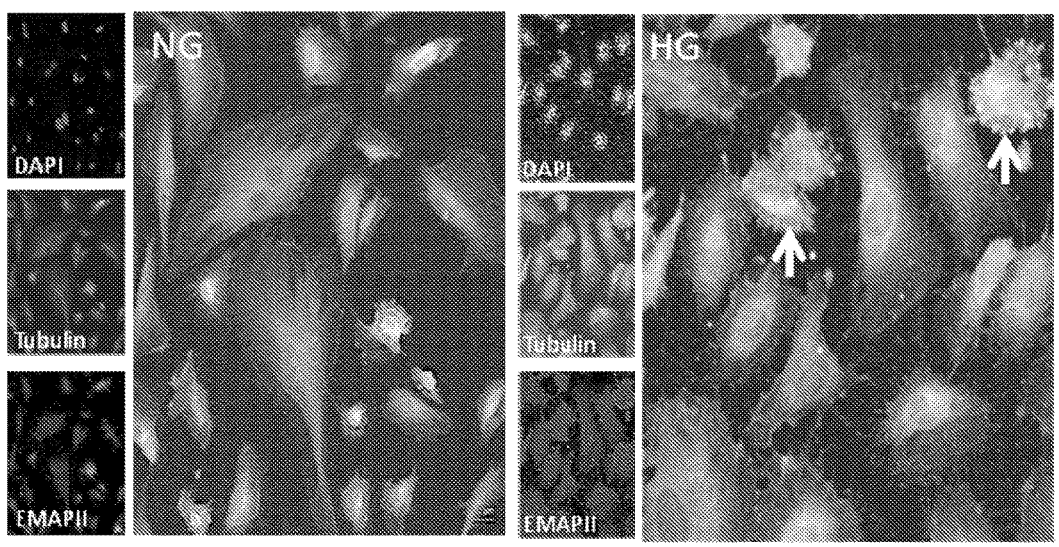
FIG. 11. shows immunofluorescence photomicrographs of HREC cells exposed to hyperglycemic or normal glucose levels and immunostained for Tubulin, EMAPII, and DAPI.

Example 10: Immunofluorescent Analysis of EMAPII and Tubulin Colocalization in Hyperglycemia HREC cells were challenged with hyperglycemic or normal glucose conditions and then fixed and immunostained for Tubulin, EMAPII, and DAPI. As shown in FIG. 11, EMAPII was upregulated in cells challenged with high glucose (HG) compared with normal glucose (NG). This increase in nuclear EMAPII accompanied depolymerization of the tubulin cytoskeleton in mid-late apoptotic cells (FIG. 11; arrows).

Figure 12:
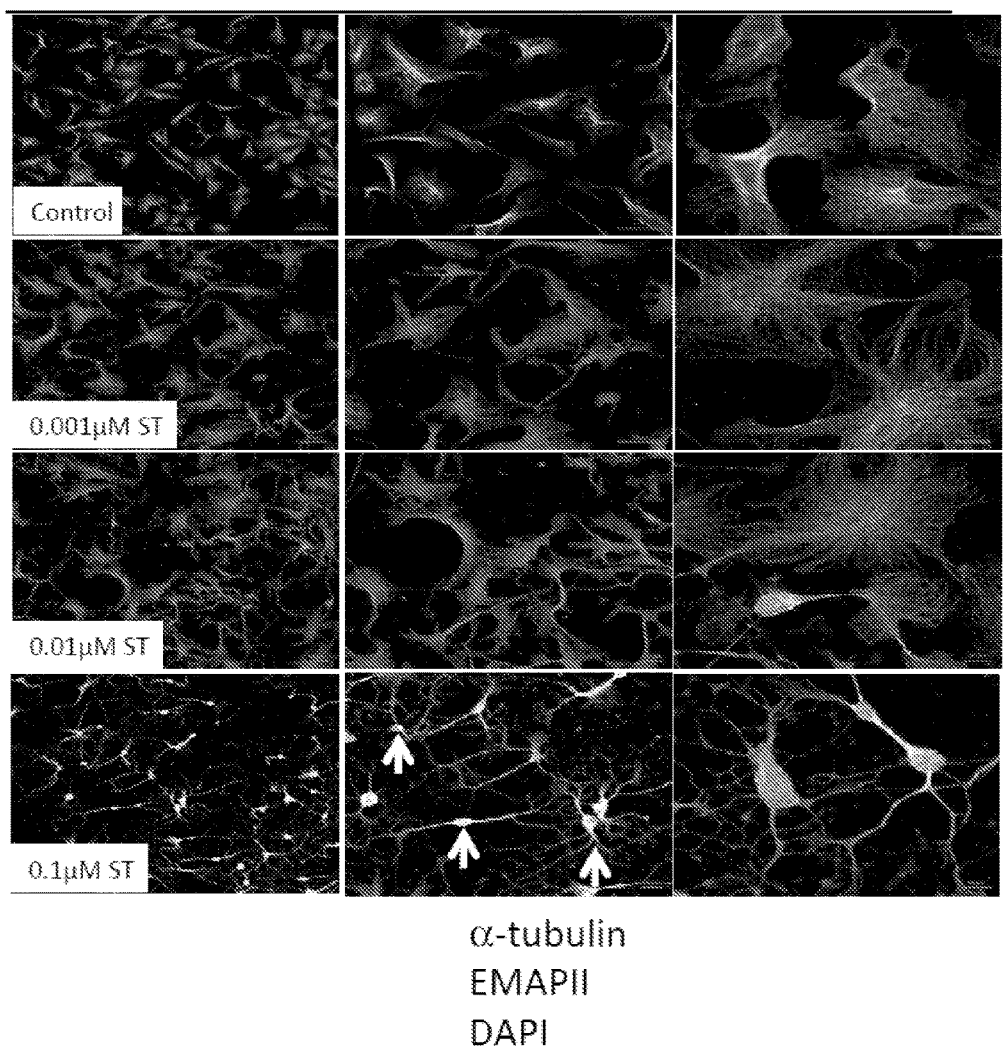
FIG. 12. shows immunofluorescence photomicrographs of HREC cells exposed to various concentrations of staurosporine and immunostained for Tubulin, EMAPII, and DAPI. Arrows indicate colocalization in late apoptosis of EMAPII with the nuclear marker DAPI.

Example 10: Immunofluorescent Analysis of EMAPII and Tubulin Colocalization Under Progressive Stages of Apoptosis Staurosporin-treated HREC cells were stained for Tubulin, EMAPII and DAPI. Early-apoptotic cells have EMAPII mostly in the cytoplasm, with no significant evidence of Tubulin depolymerization. In mid-apoptotic cells, EMAPII staining is mostly colocalized with tubulin. In late stage apoptosis, EMAPII significantly translocated into the nucleus (FIG. 12, arrows) accompanied by complete Tubulin depolymerization.

Example 11: Confocal Microscopy Confirms Nuclear Translocation of EMAPII

Figure 13:
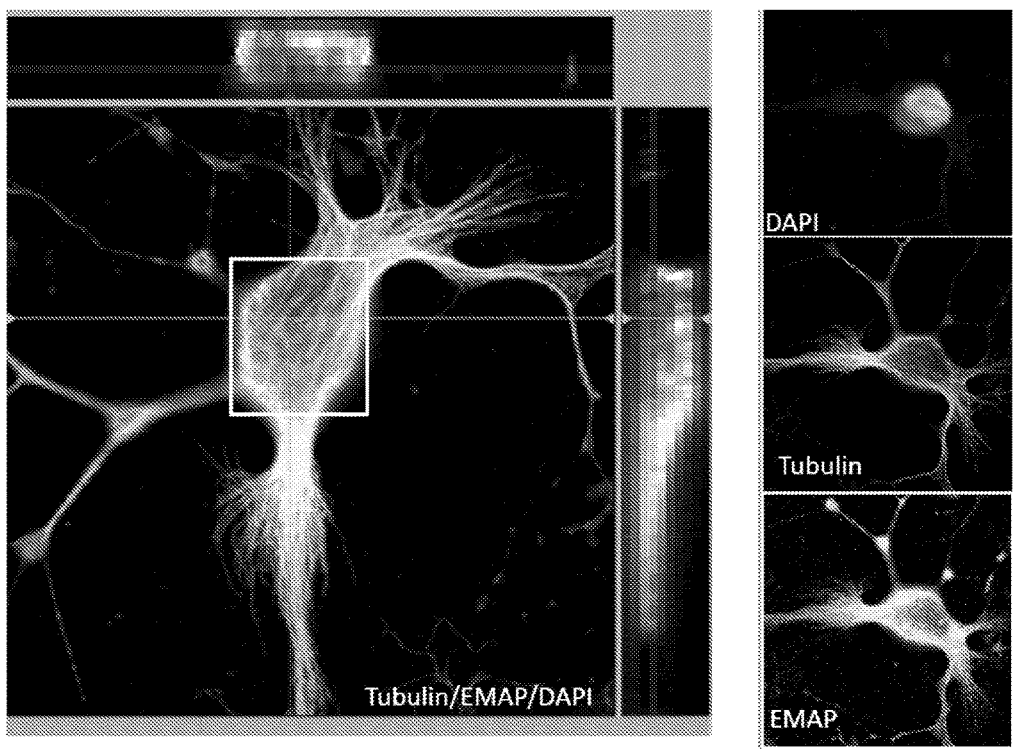
FIG. 13. shows confocal immunofluorescence photomicrographs of HREC cells exposed to various concentrations of staurosporine and immunostained for Tubulin, EMAPII, and DAPI. An orthogonal view (to the right of large panel) confirms nuclear translocation of EMAPII.

In late stage apoptosis, EMAPII significantly translocated into the nucleus accompanied by complete Tubulin depolymerization as evidenced by an orthogonal view by acquired by confocal microscopy (FIG. 13).

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

---

I claim:

1. A method of treating an individual having diabetic retinopathy, the method comprising the step of:
administering to the individual a therapeutically effective amount of an endothelial monocyte-activating polypeptide II (EMAPII) neutralizing monoclonal antibody that specifically binds to an epitope consisting of SEQ ID NO:12 and inhibits the binding of human EMAPII to CXCR3, wherein the monoclonal antibody comprises heavy chain hypervariable regions SEQ ID NO:5, SEQ ID NO:6, and SEQ ID NO:7; and light chain hypervariable regions SEQ ID NO:8, SEQ ID NO:9, and SEQ ID NO:10, whereby diabetic retinopathy is treated in the individual.

2. A method of treating an individual suspected of having diabetic retinopathy, the method comprising the step of:
administering to the individual a composition comprising a therapeutically effective amount of an EMAPII neutralizing monoclonal antibody that specifically binds to an epitope consisting of SEQ ID NO:12 and inhibits the binding of human EMAPII to CXCR3, wherein the individual is pre-determined to have an elevated level of EMAPII expression, and wherein the monoclonal antibody comprises heavy chain hypervariable regions SEQ ID NO:5, SEQ ID NO:6, and SEQ ID NO:7; and light chain hypervariable regions SEQ ID NO:8, SEQ ID NO:9, and SEQ ID:10, whereby diabetic retinopathy is treated in the individual.

* * * * *

UNITED STATES PATENT AND TRADEMARK OFFICE
CERTIFICATE OF CORRECTION

PATENT NO. : 10,132,815 B2  
APPLICATION NO. : 14/767111  
DATED : November 20, 2018  
INVENTOR(S) : Shekhar Raja Gangaraju Page 1 of 1

It is certified that error appears in the above-identified patent and that said Letters Patent is hereby corrected as shown below:

In the Specification

Column 18, Line 37, "(sRNA)" should be --(siRNA)--.

Column 18, Line 42, "(sRNA)" should be --(siRNA)--.

Column 18, Line 45, "(sRNA)" should be --(siRNA)--.

Column 18, Line 47, "(sRNA)" should be --(siRNA)--.

Signed and Sealed this  
Twenty-fifth Day of December, 2018

Andrei Iancu  
*Director of the United States Patent and Trademark Office*